(12) United States Patent
Ideker et al.

(10) Patent No.: US 7,162,298 B2
(45) Date of Patent: *Jan. 9, 2007

(54) DEVICES FOR DETECTING THE PRESENCE OF CARDIAC ACTIVITY FOLLOWING ADMINISTRATION OF DEFIBRILLATION THERAPY

(75) Inventors: Raymond E. Ideker, Birmingham, AL (US); Gregory P. Walcott, Wilsonville, AL (US)

(73) Assignee: UAB Research Foundation, Birmingham, AL (US)

( * ) Notice: Subject to any disclaimer, the term of this patent is extended or adjusted under 35 U.S.C. 154(b) by 696 days.

This patent is subject to a terminal disclaimer.

(21) Appl. No.: 10/238,340

(22) Filed: Sep. 10, 2002

(65) Prior Publication Data

US 2004/0049117 A1    Mar. 11, 2004

(51) Int. Cl.
*A61N 1/39* (2006.01)
(52) U.S. Cl. .................. 607/4; 607/5; 607/13
(58) Field of Classification Search .............. 607/4, 607/5, 6, 13, 9, 28, 14; 600/518, 509
See application file for complete search history.

(56) References Cited

U.S. PATENT DOCUMENTS

| | | | |
|---|---|---|---|
| 3,825,015 A | 7/1974 | Berkovits | 128/404 |
| 3,995,623 A | 12/1976 | Blake et al. | 128/2.06 E |
| 4,355,646 A | 10/1982 | Kallok et al. | 128/786 |
| 4,365,639 A | 12/1982 | Goldreyer | 128/786 |
| 4,444,195 A | 4/1984 | Gold | 128/642 |
| 4,499,907 A | 2/1985 | Kallok et al. | 128/786 |
| 4,559,946 A | 12/1985 | Mower | 128/419 D |
| 4,567,901 A | 2/1986 | Harris | 128/786 |
| 4,637,397 A | 1/1987 | Jones et al. | 128/419 D |
| 4,643,201 A | 2/1987 | Stokes | 128/786 |
| 4,677,986 A * | 7/1987 | DeCote, Jr. | 600/510 |
| 4,693,253 A | 9/1987 | Adams | 128/419 D |
| 4,708,145 A | 11/1987 | Tacker, Jr. et al. | 128/419 D |
| 4,800,883 A | 1/1989 | Winstrom | 128/419 D |
| 4,827,936 A * | 5/1989 | Pless et al. | 607/4 |
| 4,830,006 A * | 5/1989 | Haluska et al. | 607/4 |
| 4,850,357 A | 7/1989 | Bach, Jr. | 128/419 D |
| 4,901,725 A | 2/1990 | Nappholz et al. | 128/419 |
| 4,928,688 A | 5/1990 | Mower | 128/419 |
| 5,107,834 A | 4/1992 | Ideker et al. | 128/419 D |
| 5,165,403 A | 11/1992 | Mehra | 128/419 |
| 5,172,690 A * | 12/1992 | Nappholz et al. | 607/13 |
| 5,184,616 A | 2/1993 | Weiss | 128/419 |
| 5,201,808 A | 4/1993 | Steinhaus et al. | 128/419 |

(Continued)

FOREIGN PATENT DOCUMENTS

EP    0095726 B1    2/1988

(Continued)

OTHER PUBLICATIONS

Allessie et al., "Regional control of atrial fibrillation by rapid pacing in concious dogs," *Circulation* 1991;84:1689-1697.

(Continued)

*Primary Examiner*—Kennedy Schaetzle
(74) *Attorney, Agent, or Firm*—Myers Bigel Sibley & Sajovec

(57) ABSTRACT

The present invention provides systems, methods and computer program products for detecting the presence of cardiac activity in a patient. The present invention includes a detector circuit that is configured to detect the influence of a first defibrillation shock on the patient immediately subsequent to termination of a first defibrillation shock.

113 Claims, 9 Drawing Sheets

U.S. PATENT DOCUMENTS

| | | | |
|---|---|---|---|
| 5,209,229 A | 5/1993 | Gilli | 128/419 |
| 5,224,476 A | 7/1993 | Ideker et al. | 128/419 D |
| 5,230,337 A | 7/1993 | Dahl et al. | 607/5 |
| 5,235,977 A | 8/1993 | Hirschberg et al. | 607/5 |
| 5,235,978 A | 8/1993 | Hirschberg et al. | 607/5 |
| 5,251,624 A | 10/1993 | Bocek et al. | 607/6 |
| 5,265,600 A * | 11/1993 | Adams et al. | 607/4 |
| 5,267,559 A | 12/1993 | Jin et al. | 128/419 D |
| 5,269,298 A | 12/1993 | Adams et al. | 128/419 D |
| 5,269,319 A | 12/1993 | Schulte et al. | 128/786 |
| 5,282,836 A | 2/1994 | Kreyenhagen et al. | 607/4 |
| 5,292,338 A | 3/1994 | Bardy | 607/5 |
| 5,303,702 A | 4/1994 | Bonnet et al. | 607/20 |
| 5,304,139 A | 4/1994 | Adams et al. | 607/122 |
| 5,304,218 A | 4/1994 | Alferness | 607/122 |
| 5,312,444 A | 5/1994 | Bocek et al. | 607/5 |
| 5,313,953 A | 5/1994 | Yomtov et al. | 600/508 |
| 5,314,430 A | 5/1994 | Bardy | 607/5 |
| 5,324,309 A | 6/1994 | Kallok | 607/5 |
| 5,331,966 A | 7/1994 | Bennett et al. | 128/696 |
| 5,332,400 A | 7/1994 | Alferness | 607/5 |
| 5,344,430 A | 9/1994 | Berg et al. | 607/8 |
| 5,348,021 A | 9/1994 | Adams et al. | 128/708 |
| 5,350,401 A * | 9/1994 | Levine | 607/4 |
| 5,350,402 A | 9/1994 | Infinger et al. | 607/5 |
| 5,366,485 A | 11/1994 | Kroll et al. | 607/5 |
| 5,366,486 A | 11/1994 | Zipes et al. | 607/5 |
| 5,376,104 A * | 12/1994 | Sakai et al. | 607/5 |
| 5,387,233 A | 2/1995 | Alferness et al. | 607/126 |
| 5,395,373 A | 3/1995 | Ayers | 607/8 |
| 5,403,351 A | 4/1995 | Saksena | 607/4 |
| 5,403,354 A | 4/1995 | Adams et al. | 607/5 |
| 5,405,375 A | 4/1995 | Ayers et al. | 607/122 |
| 5,411,527 A | 5/1995 | Alt | 607/5 |
| 5,423,772 A | 6/1995 | Lurie et al. | 607/282 |
| 5,431,681 A | 7/1995 | Helland | 607/4 |
| 5,431,682 A | 7/1995 | Hedberg | 607/5 |
| 5,431,683 A | 7/1995 | Bowald et al. | 607/5 |
| 5,433,729 A | 7/1995 | Adams et al. | 607/5 |
| 5,433,730 A | 7/1995 | Alt | 607/5 |
| 5,441,519 A | 8/1995 | Sears | 607/5 |
| 5,443,491 A | 8/1995 | Snichelotto | 607/122 |
| 5,447,519 A | 9/1995 | Peterson | 607/5 |
| 5,456,706 A | 10/1995 | Pless et al. | 607/122 |
| 5,464,429 A | 11/1995 | Hedberg et al. | 607/4 |
| 5,464,432 A | 11/1995 | Infinger et al. | 607/5 |
| 5,470,348 A | 11/1995 | Neubauer et al. | 607/68 |
| 5,476,498 A | 12/1995 | Ayers | 607/122 |
| 5,476,499 A | 12/1995 | Hirschberg | 607/123 |
| 5,486,199 A | 1/1996 | Kim et al. | 607/5 |
| 5,487,753 A | 1/1996 | MacCarter et al. | 607/17 |
| 5,489,293 A | 2/1996 | Pless et al. | 607/5 |
| 5,522,853 A | 6/1996 | Kroll | 607/5 |
| 5,531,764 A | 7/1996 | Adams et al. | 607/5 |
| 5,554,176 A | 9/1996 | Maddison et al. | 607/9 |
| 5,560,369 A | 10/1996 | McClure et al. | 128/704 |
| 5,578,064 A | 11/1996 | Prutchi | 607/19 |
| 5,584,865 A | 12/1996 | Hirschberg et al. | 607/5 |
| 5,601,608 A * | 2/1997 | Mouchawar | 607/5 |
| 5,609,621 A | 3/1997 | Bonner | 607/122 |
| 5,620,471 A | 4/1997 | Duncan | 607/14 |
| 5,683,429 A | 11/1997 | Mehra | 602/14 |
| 5,690,683 A * | 11/1997 | Haefner et al. | 607/4 |
| 5,697,953 A | 12/1997 | Kroll et al. | 607/5 |
| 5,718,718 A | 2/1998 | Kroll et al. | 607/5 |
| 5,800,469 A | 9/1998 | Nappholz | 607/18 |
| 5,800,470 A | 9/1998 | Stein et al. | 607/20 |
| 5,861,012 A | 1/1999 | Stroebel | 607/28 |
| 5,978,704 A | 11/1999 | Ideker et al. | 607/123 |
| 5,978,705 A | 11/1999 | KenKnight et al. | 607/5 |
| 5,987,354 A | 11/1999 | Cooper et al. | 607/5 |
| 6,002,962 A | 12/1999 | Huang et al. | 607/5 |
| 6,006,131 A | 12/1999 | Cooper et al. | 607/5 |
| 6,148,230 A | 11/2000 | KenKnight | 600/516 |
| 6,275,730 B1 | 8/2001 | KenKnight et al. | 607/5 |
| 6,285,907 B1 | 9/2001 | Kramer et al. | 607/9 |
| 6,327,500 B1 | 12/2001 | Cooper et al. | 607/5 |
| 6,445,951 B1 * | 9/2002 | Mouchawar | 607/28 |
| 2004/0049118 A1 * | 3/2004 | Ideker et al. | 600/510 |

FOREIGN PATENT DOCUMENTS

| | | |
|---|---|---|
| EP | 0472 411 A1 | 2/1992 |
| EP | 0554 208 A2 | 8/1993 |
| EP | 0 601 340 A1 | 6/1994 |
| EP | 0 653 223 A2 | 10/1994 |
| EP | 0804938 A2 | 11/1997 |
| WO | WO96/23546 | 8/1996 |
| WO | WO 97/01373 | 1/1997 |
| WO | WO99/65561 | 12/1999 |

OTHER PUBLICATIONS

Capucci et al., "Capture window in human atrial fibrillation: evidence of an excitable gap," *I Cardiovasc Electrophysiol* 1999;10:319-327.

Cooper et al., "Internal Cardioversion of Atrial Fibrillation in Sheep," Atrial Fibrillation: Mechanisms and Therapeutic Strategies, pp. 325-332 (1994).

Cooper et al., "Internal Cardioversion of Atrial Fibrillation in Sheep," Circulation, vol. 87, No. 5, May 1993, pp. 1673-1685.

Daoud et al. "Response of Type I atrial fibrillation to atrial pacing in humans," Circulation 1996;94:1036-1040.

Feeser et al., "Strength-Duration and Probability of Success Curves for Defibrillation with Biphasic Waveforms," *Circulation*, vol. 82, No. 6, Dec. 1990, pp. 2128-2141.

Garcia-Calvo et al., "The effects of selective stellate ganglion manipulation on ventricular refractoriness and excitability," PACE, 1992;15:1492-1503.

Huang et al., "Evolution of the organization of epicardial activation patterns during ventricular fibrillation," J Cardiovasc Electrophysiol, 1998;9:1291-1304.

KenKnight et al., "Regional capture of fibrillating ventricular myocardium: Evidence of an excitable gap," Circ Res 1995;77:849-855.

Kirchhof et al., "Regional entrainment of atrial fibrillation studied by high-resolution mapping in open-chest dogs," Circulation 1993;88:736-749.

Knisley et al., "Line stimulation parallel to myofibers enhances regional uniformity of transmembrane voltage changes in rabbit hearts," Circ Res 1997;81:229-241.

Kroll, Mark W., "A Minimal Model of the Monophasic Defibrillation Pulse," PACE, vol. 16; Apr. 1993, Part 1, pp. 769-777.

Lewalter et al., "The Low Intensity Treadmill Exercise" Protocol for Appropriate Rate Adaptive Programming of Minute Ventilation Controlled Pacemakers, PACE, 18:1374-1387 (Jul. 1995).

Lok et al.; "Clinical Shock Tolerability and Effect of Different Right Atrial Electrode Locations on Efficacy of Low Energy Human Transvenous Atrial Defibrillation Using an Implantable Lead System", *JACC* 30:5 1324-1330 (1997).

Lüderitz et al., "Nonpharmacologic Strategies for Treating Atrial Fibrillation," The American Journal of Cardiology, vol. 77, Jan. 25, 1996, pp. 45A-52A.

Neri et al.; "Internal Cardioversion of Chronic Atrial Fibrillation in Patients", *PACE* 20 2237-2242 (1997).

Opthof et al., "Dispersion of refracteries in canine ventricular myocardium: Effects of sympathetic stimulation," Circ Res 1991;68:1204-1215.

Prof. Dr. med. Eckhard Alt; "Letters to the Editor", *PACE* 21 633-634 (1998).

Province et al., "Effect of pulse train amplitude and waveform on ability to entrain fibrillating rabbit ventricle with epicardial pacing," PACE, 22:A66 (1999) (Abstract).

Qin, Hao et al., "Recurrence Patterns After Failed Defibrillation of Spontaneous Ventricular Fibrillation During Acute Ischemia,"

Supplement to Journal of the American College of Cardiology, p. 3, Mar. 6, 2002, vol. 39, No. 5 Supplement A.

Qin, Hao et al., "Difibrillation Efficacy for Spontaneous and electrically-Induced Ventricular Fibrillation During Acute Ischemia," Supplement to Circulation Journal of the American Heart Association, #2125, 2000.

Qin, Hao et al., "Impact of Myocardial Ischemia and Reperfusion on Ventricular Defibrillation Patterns, Energy Requirements, and Detection of Recovery," (Circulation 2002;105:2537) Published online before print May 6, 2002, 10.1161/01.CIR.0000016702.86180.F6.

Rogers et al., "A quantitative framework for analyzing epicardial activation patterns during ventricular fibrillation," Ann Biomed Eng 1997; 25:749-760.

Rogers et al., "Recurrent wavefront morphologies: a method for quantifying the complexity of epicardial activation patterns," Ann Biomed Eng 1997; 25:761-768.

Rollins et al., "Macintosh based programmable cardiac stimulatr," J Am Coll Cardiol, 15:261A (1990) Abstract.

Vander et al. "*Human Physiology—The Mechanisms of Body Functio*," pp. 230-236, Jan. 1985.

Wharton et al., "Cardiac potential and potential gradient fields generated by single, combined, and sequential shocks during ventricular defibrillation," Circulation 1992; 85:1510-1523.

Wright et al., "Cardiac Rhythm Management Laboratory: *In Vivo* Study Protocol, Internal Atrial Defibrillation in Sheep Using Sequential Biphasic Waveforms," CRM Laboratory, University of Alabama—Birmingham Medical Center, Oct. 1995.

PCT International Search Report, International Application No. PCT/US01/47195 dated Jul. 23, 2002.

Laxer, Cary et al., *The Use of Computer Animation of Mapped Cardiac Potentials in Studying Electrical Conduction Properties of Arrhythmias*, IEEE, 1991, pp. 23-26.

Wolf, P. D. et al., *A 528 Channel System for the Acquisition and Display of Defibrillation and Electrocardiographic Potentials*, IEEE, 1993, pp. 125-128.

Lammers, W. J.E.P. et al., *The use of fibrillation cycle length to determine spatial dispersion in electrophysiological properties and to characterize the underlying mechanism of fibrillation*, New Trends In Arrhythmias, vol. II, N.1, Jan.-Mar. 1986, pp. 109-112.

* cited by examiner

DEVICES FOR DETECTING THE PRESENCE OF CARDIAC ACTIVITY FOLLOWING ADMINISTRATION OF DEFIBRILLATION THERAPY

RELATED APPLICATION

This application is related to co-owned and co-assigned U.S. patent application Ser. No. 10/238,342 entitled Methods, Systems and Computer Program Products for Treating Fibrillation in a Patient Based on the Presence of Fibrillation Following Administration of Defibrillation Therapy filed concurrently herewith, the disclosure of which is hereby incorporated herein by reference.

FIELD OF THE INVENTION

The present invention relates to detection of cardiac activity and, more particularly, to detecting fibrillation in the heart of a patient.

BACKGROUND OF THE INVENTION

The heart is a muscular organ that is covered by a fibrous sac known as the pericardium. The space between the pericardium and the muscular organ is called the pericardial space. The walls of the heart are substantially formed from muscle (the myocardium) that differs from either skeletal or smooth muscle. The heart comprises atria and ventricles, each of which is composed of layers of myocardium that are formed to encase the blood-filled chambers. In operation, when the walls of a chamber contract, they come together similar to a squeezing fist. This contraction of the cardiac muscle is triggered by depolarization of the muscle membrane. To operate properly, the muscle contractions should be coordinated.

If the muscle contractions are not coordinated within the ventricles, blood may be sloshed back and forth within the ventricular cavities instead of being ejected into the aorta and pulmonary arteries. Thus, the complex muscle masses forming the ventricular pumps should contract substantially simultaneously for efficient pumping.

The heart is able to achieve this coordination because of (a) the tight junctions formed between adjacent cardiac fibers (the fibers are joined end to end at structures known as intercalated disks, which provide the points or junctions) which allow action potentials to be transmitted from one cardiac cell to another; and (b) the specialized muscle fibers in certain areas of the heart which provide the conducting system for proper excitation of the heart. The specialized fibers are in contact with fibers of the cardiac muscles to form gap junctions, which permit passage of action potentials from one cell to another. The specialized conduction system is configured, in normal operation, to provide a rapid and coordinated spread of excitation.

Cardiac muscle cells are autorhythmic, i.e., capable of spontaneous, rhythmical self-excitation. The sinoatrial (SA) node is the normal pacemaker for the entire heart or smooth muscle, and it is from this region that the excitation wave starts; it then moves or propagates through the remainder of the myocardium in a synchronized manner. The SA node region of the heart contains a small mass of specialized myocardial cells in the right atrial wall near the entrance of the superior vena cava that have a fast inherent rhythm, which allows the SA node to be the normal pacemaker. In unusual circumstances, other regions of the heart can become more excitable and provide a faster spontaneous rhythm. In this situation, this other region can become the pacemaker and the rhythm for the entire heart.

In normal operation, the cells of the SA node make contact with the surrounding atrial myocardium fibers. Thus, from the SA node, a wave of excitation spreads throughout the right atrium along the atrial myocardial cells via the gap junctions. In addition, the atrial tissue directs the impulse from the SA node directly to the left atrium, to simultaneously contract both atria.

The excitation wave then is distributed to the ventricles by way of a second small mass of specialized cells located at the base of the right atrium near the wall between the ventricles (the atrioventricular (AV) node). The AV node is configured to delay the propagation of action potentials (the wavefront) by about 0.1 second, to allow the atria to contract and empty the blood into the ventricle before ventricular contraction. The wavefront is then quickly dispersed along the specialized conducting fibers (down the interventricular septum to the ventricular free walls) and then through unspecialized (typical) myocardial fibers in the remaining myocardium.

The pumping of blood includes alternate periods of contraction and relaxation. The cardiac muscle has a relatively long refractory period (on the order of about 250 ms in humans). This refractory period is a time during which the membrane is insensitive to stimulus (either totally unable to propagate an excitation wave or only able to do so upon exposure to an increased level of stimulation).

Heart function may be decreased in certain conditions in heart failure. In such conditions, it may be possible to increase synchronization of electrical activity that increases the muscular contraction synchronization, thereby improving cardiac function.

During ventricullar fibrillation (VF) a number of independent activation wavefronts propagate simultaneously through the mycodardium. The propagation of these wavefronts may result in uncoordinated activity from the heart that may result in reduced or impaired cardiac function. Resuscitation attempts for cardiac arrest caused by VF include defibrillation shock. The defibrillation shock is intended to break up the propagation of the independent activation wavefronts to allow normal activation. If the fibrillation is halted by the first defibrillation shock applied to the affected area of the heart, no further action is typically required. If, on the other hand, the fibrillation is not halted by the first electric shock, the size of the shock is typically increased and a second defibrillation shock may be applied to the heart. Typically, this process is repeated until normal activity results. Three potentially problematic outcomes may result from application of a defibrillation shock. First, the defibrillation shock may fail to halt the fibrillation. Second, the defibrillation shock may halt the fibrillation but fibrillation may then re-occur in the next few seconds or minutes. Third, the defibrillation shock may be successful and cardiac electrical activity may return after the shock but cardiac function is either absent or greatly reduced. This third condition may be referred to as pulseless electrical activity (PEA).

The cause of atrial fibrillation or VF may be an indication of the strength of the defibrillation shock needed to halt the contraction of the heart muscle. For example, it is commonly thought that the defibrillation threshold, i.e. the strength of the defibrillation shock, is elevated when ventricular fibrillation occurs spontaneously in the presence of constriction and/or obstruction of a blood vessel (i.e. acute ischemia). Patients suffering from this condition will often have to be shocked using very high voltages. Exposing the heart muscle to these high voltages may damage the heart and cause persistent malfunction. The high voltage shocks may also lead to an arrhythmia of the heart or even death.

Thus, improvements may be needed in the treatment of fibrillation, either ventricular or atrial, that may reduce the occurrence of one or more of these problematic results. In particular, improvements may be needed to avoid damaging the heart.

SUMMARY OF THE INVENTION

Embodiments of the present invention provide systems, methods and computer program products for detecting the presence of cardiac activity in a patient. Embodiments of the present invention include a detector circuit that is configured to detect the influence of a first defibrillation shock on the patient immediately subsequent to termination of a first defibrillation shock.

In some embodiments of the present invention, the detector circuit may be configured to detect the influence of the first defibrillation shock on the patient within about two seconds of termination of the first defibrillation shock.

Further embodiments of the present invention may include a defibrillator circuit configured to administer the first defibrillation shock to the patient and/or a recorder circuit configured to record the influence of the first defibrillation shock on the patient immediately subsequent to termination of the first defibrillation shock. The recorder circuit may be configured to record the influence of the first defibrillation shock on the patient within about two seconds of termination of the first defibrillation shock.

Still further embodiments of the present invention may include an isolation circuit configured to electrically isolate the detector circuit from the defibrillation shock. The isolation circuit may be configured to electrically isolate the detector circuit from the defibrillation shock from about 0.3 seconds before initiation of the first defibrillation shock to about 0.3 seconds after termination of the first defibrillation shock. In some embodiments the isolation circuit is one of a relay and a switch.

In some embodiments of the present invention, the defibrillator circuit may include a plurality of electrodes. The isolation circuit may be further configured to decouple the plurality of electrodes of the defibrillator circuit from the detector circuit before initiation of the first defibrillation shock until after termination of the first defibrillation shock.

In further embodiments of the present invention, the isolation circuit may be further configured to decouple the plurality of electrodes of the defibrillator circuit from the recorder circuit before initiation of the first defibrillation shock until after termination of the first defibrillation shock.

In still further embodiments of the present invention, the detector circuit may include at least one amplifier and the isolation circuit may be configured to decouple the at least one amplifier from the defibrillation circuit, for example, by isolating a sensor lead from the detector circuit. The isolation circuit may be further configured to pass a current through the detector circuit. In some embodiments the detector circuit may include at least one amplifier having a large dynamic range associated therewith.

In some embodiments of the present invention, the detector circuit, the defibrillator circuit, the recorder circuit and the isolation circuit may be configured to be disposed within a single implantable housing for implantation in the patient. The implantable housing may be an implantable defibrillator. The isolation circuit may further include an insulator module that is configured to insulate the detector circuit within the implantable defibrillator from the first defibrillation shock.

Alternatively, the detector circuit, the defibrillator circuit, the recorder circuit and the isolation circuit may be configured to be disposed within a single housing that is external to the patient. The single housing may be an external defibrillator. Finally, the detector circuit, the defibrillator circuit, the recorder circuit and the isolation circuit may be respective separate devices. Furthermore, at least one of the detector circuit, the defibrillator circuit, the recorder circuit and the isolation circuit may be configured to be disposed within an implantable housing for implantation within the patient and at least one of the detector circuit, the defibrillator circuit, the recorder circuit and the isolation circuit may be configured to be external to the patient.

In further embodiments of the present invention the defibrillator circuit may be further configured to indicate termination of the defibrillation shock to the detector circuit. The detector circuit may be further configured to determine if the cardiac activity of the patient immediately subsequent to termination of a first defibrillation shock is normal cardiac activity.

Still further embodiments of the present invention include a controller circuit configured to apply a pacing stimulation signal to a heart of a patient if the detector circuit determines that the cardiac activity of the patient immediately subsequent to termination of the first defibrillation shock is normal cardiac activity. The controller circuit may be configured to apply the pacing stimulation within about two seconds of termination of the defibrillation shock. The pacing stimulation signal may be pacing stimulation or paired pacing stimulation.

In some embodiments of the present invention the controller circuit is configured to detect cardiac activity of the heart associated with application of the single pacing stimulation and selectively apply paired pacing stimulation based on the detected cardiac activity. In some embodiments the controller circuit is configured to detect cardiac activity of the heart and selectively apply paired pacing stimulation based on the detected cardiac activity. In further embodiments the controller circuit is configured to detect a signal specifying application of paired pacing and selectively apply paired pacing stimulation based on the detected signal.

In further embodiments of the present invention the defibrillation shock may be applied to a heart of a patient using at least one first set of electrodes and the controller circuit may be configured to apply the pacing stimulation signal to the heart of the patient subsequent to termination of the defibrillation shock using at least one second second set of electrodes. The first set of electrodes and the second set of electrodes may be different sets of electrodes or the same set of electrodes.

In some embodiments of the present invention, the controller circuit may be further configured to selectively apply paired pacing stimulation to the heart based on at least one of receipt of an external specification and sensed variables associated with cardiac activity. The sensed variables associated with cardiac activity may include a pulse pressure below a predefined threshold. The external specification may include instruction from a healthcare provider.

In further embodiments, the controller circuit may be configured to be disposed within an implantable housing for implantation in the patient. Alternatively, the controller circuit may be configured to be external to the patient.

Some embodiments include at least one set of electrodes for application of the pacing stimulation signal to the heart of the patient. The controller circuit may be configured to apply the pacing stimulation within about one second of termination of the defibrillation shock.

In still further embodiments of the present invention the detected cardiac activity may be fibrillation and the detector circuit may be configured to detect if the fibrillation ceases immediately after termination of the first defibrillation shock and reinitiates within a predetermined time period after the first defibrillation shock.

In some embodiments the controller circuit is configured to administer a second defibrillation shock having a second shock value that is at least one of substantially equivalent to the first shock value and less than the first shock value immediately if it is determined that the fibrillation has ceased after termination of the first defibrillation shock and reinitiated within the predetermined time period.

In further embodiments the controller circuit is configured to wait a second predetermined time period if it is determined that the fibrillation ceased after termination of the first defibrillation shock and reinitiated within the first predetermined time period and determine if fibrillation ceases after termination of the second predetermined time period. The controller circuit may be further configured to administer a third defibrillation shock having a third shock value that is at least one of substantially equivalent to the first shock value and less than the first shock value after the second predetermined time period if it is determined that the fibrillation has not ceased after termination of the second predetermined time period.

In still further embodiments of the present invention, the controller circuit may be configured to administer cardiopulmonary resuscitation (CPR) for a second predetermined time period if the fibrillation ceased after termination of the first defibrillation shock and reinitiated within the first predetermined time period and determine if the cardiac activity has been influenced by the administration of CPR. The controller circuit may be further configured to administer a third defibrillation shock having a third shock value that is at least one of substantially equivalent to the first shock value and less than the first shock value after termination of the second predetermined time period if it is determined that the fibrillation activity has not been influenced by the administration of CPR during the second predetermined time period.

In some embodiments of the present invention, the controller circuit is configured to administer a second defibrillation shock having a second shock value that is higher than the first shock value at the second time if the fibrillation is not influenced by the first defibrillation shock immediately after termination of the first defibrillation shock.

In further embodiments of the present invention, the controller circuit may be configured to detect cardiac activity and/or function of the heart and select a type of pacing stimulation to apply to the heart of the patient subsequent to termination of the defibrillation shock based on the detected cardiac activity and/or function. The selected type of pacing may be applied to the patient's heart. The cardiac activity and/or function may be detected before or after applying the defibrillation shock to a heart of the patient. The selected type of pacing stimulation may include single pacing stimulation, paired pacing stimulation and/or a combination of the two.

In still further embodiments of the present invention, the controller circuit may be configured to inhibit application of the pacing stimulation signal based on the detection of cardiac activity. The detected cardiac activity may include at least one of blood pressure and/or spontaneous electrical activity.

As will be appreciated by those of skill in the art in light of the present disclosure, the present invention may be embodied as systems, methods and/or computer program products.

DETAILED DESCRIPTION OF THE PRESENT INVENTION

Figure 1:
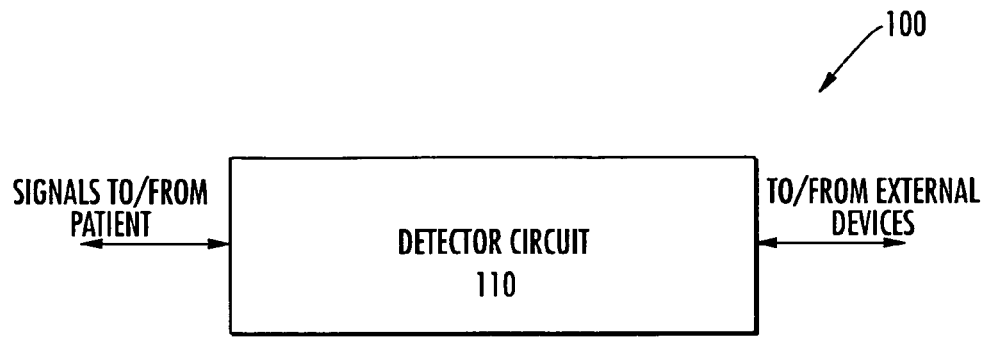
FIG. 1 is a block diagram illustrating detectors according to embodiments of the present invention.

The present invention will now be described more fully hereinafter with reference to the accompanying figures, in which embodiments of the invention are shown. This invention may, however, be embodied in many different forms and should not be construed as limited to the embodiments set forth herein.

Like numbers refer to like elements throughout. In the figures, layers, components, or features may be exaggerated for clarity.

The present invention may be used for treating cardiac malfunction, for example, atrial or ventricular fibrillation, so as to induce normal cardiac function. Subjects according to the present invention can be any animal subject, are preferably mammalian subjects (e.g., humans, canines, felines, bovines, caprines, ovines, equines, rodents, porcines, and/or lagomorphs), and more preferably are human subjects.

Embodiments of the present invention will be discussed below with respect to FIGS. 1 through 14. Embodiments of the present invention provide devices and/or methods for detecting the presence of cardiac activity in a patient. Certain embodiments of the present invention may include a detector circuit capable of detecting the influence of a defibrillation shock immediately subsequent to termination of the defibrillation shock. The capability to detect and/or record cardiac function so rapidly may enable new treatments and more accurate diagnosis of the conditions that may cause cardiac malfunction.

One or more sets of electrodes may be placed at one or more sites. References to an electrode herein may refer to one or more electrodes associated with a stimulation site. Accordingly, references to stimulation of an electrode or application of a stimulation signal may refer to stimulation of the one or more electrodes associated with a stimulation site or path. The various stimulation sites utilized may depend on the particular patient and/or stimulation regime. Such sites may, for example, include those described in U.S. Pat. Nos. 4,929,688 and 6,285,907, the disclosures of which are incorporated by reference herein as if set forth fully. Similarly, differing electrode configurations and locations may also be utilized with embodiments of the present invention. For example, the placement and type of electrodes may be as described in U.S. patent application Ser. No. 09/742,651 filed Dec. 21, 2000 and entitled "PACING METHODS AND DEVICES FOR TREATING CARDIAC ARRHYTHMIAS AND FIBRILLATION," the disclosure of which is incorporated herein by reference as if set forth in its entirety. Suitable commercially available electrodes may include defibrillation electrodes well known to those of skill in the art. In some embodiments, the electrodes that are adapted to reside in the heart in the vein(s) of a subject may be particularly suitable. See also, U.S. Pat. Nos. 5,107,834, 5,224,476, 5,978,704, and 6,002,962, the contents of which are hereby incorporated by reference as if recited in full herein.

The catheters or electrodes may also include sensors for measuring cardiac function. For example, a catheter may include one or more stimulation electrodes and/or sensors for sensing one or more of the onset of a treatment condition or the intrinsic cardiac cycle. See U.S. Pat. No. 5,978,704, entitled, Method and Apparatus for Treating Cardiac Arrhythmia, the contents of which are hereby incorporated by reference as if recited in full herein. Furthermore, according to embodiments of the present invention, the sensors may also include sensors for detecting indicators of cardiac function, such as, for example, measuring changes in impedance, changes in distance between electrodes and/or the rate of change of distance and/or detection of motion through, for example, use of an accelerometer. As used herein, motion refers to acceleration, velocity, displacement, integrals of acceleration, displacement and/or velocity and/or derivatives of acceleration, displacement and/or velocity.

Anatomically, the heart includes a fibrous skeleton, valves, the trunks of the aorta, the pulmonary artery, and the muscle masses (myocardium) of the cardiac chambers (i.e., right and left atria and right and left ventricles). A full description of the anatomy of the heart is included in concurrently filed and commonly assigned U.S. patent application Ser. No. 10/238,343 entitled Post-Defibrillation Pacing Methods and Devices, the disclosure of which is incorporated herein by reference.

As mentioned above, the desired sites or localized region (s) selected for placement of the electrodes, the stimulation sites, defibrillation and/or pacing the heart according to embodiments of the present invention may vary depending on the physiology or ailment of the patient and/or the particular treatment protocol employed. As such, the electrodes may be positioned in a number of regions, internal and/or external to the body, and by a number of different techniques so that they are proximate to and/or in contact with the desired localized region of the myocardium or other sites of interest. For example, electrodes may be placed directly on the surface of the patient's chest. By way of further example, one or more electrodes can be positioned in the natural lumens of the heart (atriums, ventricles, veins, arteries, etc.), or in the pericardial space, on the outer, inner surfaces of the cardiac walls, or within the thickness of the muscle walls. The electrodes may be positioned into the body of the subject by surgical techniques or by inserting them using locating catheters holding same, and the like. In some embodiments, certain electrodes are configured and sized such that each is able to contact the tissue at a respective stimulation or sensing site during the heartbeats. As used herein, "localized" refers to the electrical stimuli being delivered to a portion of the heart rather than to the entire heart.

Thus, as noted above, the defibrillation and/or pacing electrodes may be positioned in the pericardial space or other localized regions of the heart. For example, these electrode(s) can be held on a catheter and inserted into the endocardium or threaded through the heart and inserted into the veins in the heart (threaded through the OS and looped into the veins). In some embodiments, defibrillation and/or pacing of the left atrium may be performed by locating an electrode(s) to extend in a portion of the left atrium and into the pulmonary vein(s) to help eradicate or control fibrillation activation in this region. Locating one or more sets of electrodes in the pulmonary veins may be particularly suitable for the treatment of atrial fibrillation. Other exemplary placements are discussed below.

As described above, the driving force for the flow of blood in the heart comes from the active contraction of the cardiac muscle. This contraction can be detected as an electrical signal. The cardiac contraction is triggered by electrical impulses traveling in a wave propagation pattern which begins at the cells of the SA node and the surrounding atrial myocardial fibers then travels into the atria and subsequently passing through the AV node and, after a slight delay, into the ventricles. Sensing cardiac function before during and after fibrillation or other cardiac malfunction may provide data to the treatment system, for example, a defibrillation and/or pacing system (controller or cardiac monitor) that can be assessed to determine and adjust, as needed, a number of operational parameters such as, for example, when to stop the stimulation and/or the duration or intensity of the stimulation pulse(s).

The determination of these operational parameters may be useful in determining new treatments for patients suffering from certain cardiac diseases and/or malfunctions. For example, until recently it had been thought that the defibrillation threshold, i.e. the strength of the shock applied to the heart, was much higher for spontaneous ventricular fibrillation (VF) as compared with electrically induced VF. The results of an experiment in pigs revealed that the first defibrillation shock may actually halt spontaneous VF temporarily after termination of the first defibrillation shock, but VF may quickly reoccur. Thus, the defibrillation treatment at the first shock strength may be successful, but the cause of the spontaneous VF persists and therefore VF reoccurs. In this instance there would be no need to increase the defibrillation shock strength because the first shock strength was successful. This experiment is discussed in detail in article entitled *Impact of Myocardial Ischemia and Reperfusion on Ventricular Defibrillation Patterns, Energy Requirements and Detection of Recovery* by Hoa Qin, MD et al., American Heart Association, May 2002, the disclosure of which is incorporated herein by reference.

Accordingly, the cardiac data available during the period of time immediately after the termination of the defibrillation shock is important data that may lead to alternate treatment methods for patients suffering from, for example, spontaneous VF.

Conventional detectors may not be capable of detecting cardiac data immediately after the termination of the defibrillation shock because the defibrillation shock is so large, for example on the order of 2000 V for an external defibrillator, it normally requires several seconds for conventional recording systems to recover before recordings can again be made. Embodiments of the present invention provide a detector circuit capable of recording cardiac data immediately after termination of the first defibrillation shock. As used herein, the term "immediately" refers to detection or application of stimulation before a conventional electro-cardiagram can detect cardiac activity to determine if the defibrillation shock successfully halted fibrillation. Thus, for example, detection of cardiac activity or application of stimulation less than about 2 to 4 seconds after the termination of the defibrillation shock may be considered immediately after termination of the defibrillation shock. In particular embodiments of the present invention, the detection and/or stimulation occurs within about 2 seconds of termination of the defibrillation shock, in further embodiments the detection and/or stimulation occurs within about 1 second of the termination of the defibrillation shock and in still further embodiments of the present invention, the detection and/or stimulation occurs within about 0.5 seconds of the termination of the defibrillation shock.

Referring now to FIG. 1, a block diagram of a detector according to embodiments of the present invention will be discussed below. A device and/or system 100 for detecting the presence of cardiac activity in a patient according to embodiments of the present invention may include a detector 110 for detecting cardiac activity, for example, atrial and/or ventricular fibrillation and/or ventricular tachycardia, in a patient. The detector 110 may be electrically coupled to the patient, thus enabling the detector 110 to detect the influence of a first defibrillation shock on the patient immediately subsequent to termination of a first defibrillation shock. It will be understood that detectors according to embodiments of the present invention may be internal or external to the patient. Detectors according to embodiments of the present invention may also be separate devices or integrated with existing devices to provide this added functionality. As discussed above, the detector 110 can detect cardiac activity sooner than conventional systems. The cardiac data may be provided to medical personnel via, for example, a medical monitor or computer monitor external to the patient. This cardiac data may be used to provide alternate treatments to patients suffering from, for example, spontaneous VF.

It will be understood that although embodiments of the present invention are discussed with respect to spontaneous VF, the present invention should not be limited to this condition. For example, devices and methods according to embodiments of the present invention may be used to treat atrial or ventricular fibrillation as well as ventricular tachycardia (VT) of any cause. These devices and methods may also be used to treat patients experiencing coronary artery ischemia or reperfusion. Coronary artery ischemia occurs when something, for example, a blood clot or thrombus, is at least partially blocking the blood flow through the heart. Reperfusion occurs when the blockage is destroyed by the body or some external force and the blood flow is restored to normal. Initially after reperfusion, a rush of blood flows through the heart quickly bringing with it a series of changes. Both ischemia and reperfusion can cause a type of cardiac malfunction that may be addressed with treatments made possible by a detector according to embodiments of the present invention.

Figure 2A:
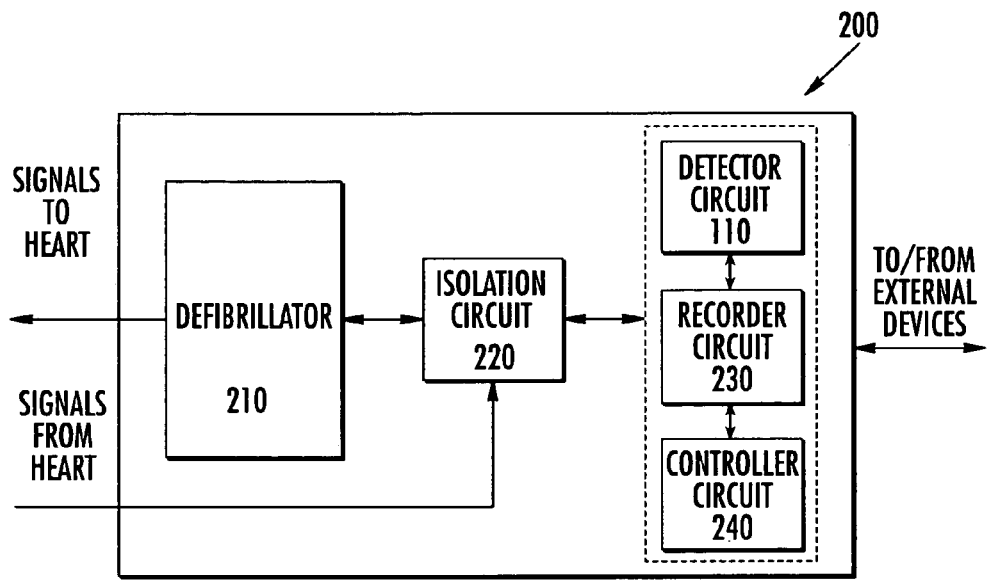
FIG. 2A is a block diagram illustrating a system including detectors according to further embodiments of the present invention.

Referring now to FIG. 2A, a block diagram of devices according to further embodiments of the present invention will be discussed. A device 200 for detecting the presence of cardiac activity in a patient may include a defibrillator 210, an isolation circuit 220, a detector circuit 110, a recorder circuit 230 and a controller circuit 240. It will be understood that although these elements are depicted as within the device 200, the present invention should not be limited to this configuration. For example, the detector circuit 110, the isolation circuit 220, the recorder circuit 230 and the controller circuit 240 may be one physical unit and may be physically separate from the defibrillator 210. Alternatively, each of the circuits may be physically separate from each other and the defibrillator 210. It will be understood that any of the circuits depicted in FIG. 2 may be external to the patient or disposed within a patient in an implantable housing.

The defibrillator 210 may have one or more sets of electrodes that are placed in particular locations or regions of the heart as discussed above. The particular location may depend on the particular application for defibrillation and/or alternate therapy. Such locations will be apparent to those of skill in the art in light of the above disclosure and will, therefore, not be described further herein. As described above, the same electrodes may be utilized for defibrillation as are used for alternate therapy, for example, pacing or burst stimulation. Alternatively, different ones or sets of electrodes may be used for defibrillation as are used for alternate therapy. Finally, combinations of common and different electrodes may be used for defibrillation and alternate therapy.

The defibrillator may be an external defibrillator or an internal defibrillator disposed within an implantable housing. The shocks produced by the defibrillator 210 may vary depending on whether the defibrillator is external or internal to the patient and the placement of the electrodes. For example, a shock produced by an external defibrillator where the electrodes are placed on the chest of the patient may be on the order of 2000 V, but a shock produced by an internal defibrillator, where the electrodes are placed in the chest, may be on the order of 700 to 800 V. With respect to an internal defibrillator, the electrodes may be placed in an upper portion of the chest. Alternatively, a first electrode may be placed in or around the left pulmonary artery and a second electrode may be placed in or around the right ventricle. The difference in shock strength may be due, in part, to the fact that the internal defibrillator is placed inside the patient either in the heart itself or in proximity thereto. As discussed above, it will be understood that the defibrillator may be either internal or external to the patient. Similarly, the electrodes may be either internal or external to the patient. Accordingly, any combination of these internal and/or external devices may be used in conformity with the teachings of the present invention.

The detector circuit 110 detects the influence of the defibrillation shock administered by the defibrillator 210. The detector circuit may include a plurality of sensor leads provided to detect cardiac function immediately after termination of a defibrillation shock administered by the defibrillator 210. As discussed above, conventional detectors are typically not capable of detecting cardiac data immediately after termination of the defibrillation shock because these detectors are typically incapable of recovering from the signals produced by the defibrillator 210. Embodiments of the present invention include an isolation circuit 220. The isolation circuit 220 isolates the detector circuit 110 from the defibrillator 210 just before, during and/or just after the defibrillation shock. For example the isolation circuit 220 may isolate the detector circuit 110 from about 0.3 seconds before the delivery of the fibrillation shock to about 0.3 seconds after the termination of the fibrillation shock. The isolation circuit 220 may disconnect the sensor leads of the detector circuit 110 before, during and after application of the defibrillation shock. The isolation of the detector circuit 110 enables the detector circuit 110 to recover quickly and to detect the influence of the defibrillation shock on the patient immediately after termination of the defibrillation shock. Examples of some embodiments of the isolation circuit 220 are illustrated in FIGS. 2B and 2C.

Figure 2B:
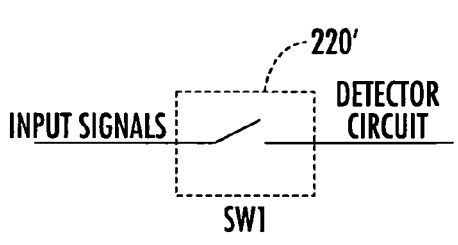
FIG. 2B is a block diagram illustrating embodiments of the isolation circuit according to embodiments of the present invention.
Figure 2C:
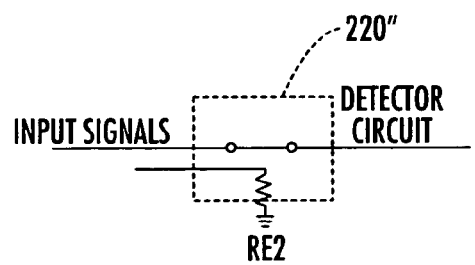
FIG. 2C is a block diagram illustrating further embodiments of the isolation circuit according to embodiments of the present invention.

For example, in some embodiments of the present invention the isolation circuit 220' may take the form a switch SW1 as illustrated in FIG. 2B. The switch SW1 may be electrically coupled to the defibrillator 210 and may be configured to open before the defibrillation shock and/or close when the defibrillation shock is terminated, for example, isolating the sensor leads from the high voltage of the defibrillation shock. Such opening and closing may be manually performed or automatically performed. Alternatively, in some embodiments of the present invention the isolation circuit 220 may take the form a relay RE2 as illustrated in FIG. 2C. The relay RE2 may be electrically coupled to the defibrillator 210 and may be configured to decouple the defibrillator 210 from the sensor leads of the detector circuit 110 before, during and/or after the defibrillation shock. Alternatively, the isolation circuit 220 may take the form of any element that decouples the detector circuit 110 from the defibrillator 210 during application of the defibrillation shock.

Further embodiments of the isolation circuit 220 will be discussed below. In some embodiments of the present invention the isolation circuit 220 may be configured to decouple a plurality of electrodes of the defibrillator 210 from the detector circuit 110 before, during and after the defibrillation shock. As discussed above, the detector circuit 110 may be decoupled less than about 0.3 seconds before initiation of the defibrillation shock until about less than 0.3 seconds after the termination of the defibrillation shock.

In some embodiments of the present invention the detector circuit 110 may include at least one amplifier. The isolation circuit 220 may be configured to decouple the at least one amplifier from the electrodes to enable the detection and/or recordation of fibrillation signals immediately after the termination defibrillation shock. In further embodiments of the present invention the isolation circuit 220 may include a plurality of filters that enable the detector circuit 110 to detect the influence of the defibrillation therapy immediately after termination of the defibrillation shock of the defibrillator 210. In still further embodiments the isolation circuit 220 may be configured to provide a current to the detector circuit 110 that may remove any changes in polarization potential induced by the defibrillation shock of the defibrillator 210.

It will be understood that although isolation of the detector circuit 110 is provided herein using an isolation circuit, embodiments of the present invention should not be limited to this configuration. It is possible to isolate the detector circuit 110 by designing the circuit to withstand the strength of the defibrillation shock rather than isolating the detector circuit from the defibrillation shock. For example, the material selected for a plurality of detecting/recording electrodes may have polarization potentials that are not typically influenced by the strength of a typical defibrillation shock of the defibrillator 210. For Example, these materials may include silver or silver chloride. Alternatively, the detector circuit 110 may include at least one amplifier configured to have a large dynamic range associated therewith that may enable the detector circuit 110 to withstand the shock produced by the defibrillator 210 without becoming saturated.

It will be understood that the detector circuit 110 according to embodiments of the present invention may be included as part of the defibrillator 210. As discussed above, the defibrillator may be an external defibrillator or an internal defibrillator disposed within the patient. An external defibrillator may be used to counteract the atrial or ventricular fibrillation by the application of electroshock to the heart directly through electrodes placed on the chest. Alternatively, an internal defibrillator may be implanted into the chest in the heart or proximate thereto or placed inside the chest on probes. Due to the fact that the electrodes of an internal defibrillator are in close proximity or direct contact with the heart, the voltage produced by an internal defibrillator is typically smaller than the voltage produced by an external defibrillator. For example, an internal defibrillator may apply a voltage of about 700 to about 800 V, whereas an external defibrillator may apply a voltage on the order of about 2000 Volts.

Furthermore, if the detector circuit 110 of the present invention is disposed within an internal defibrillator that is placed in the chest of a patient, the fibrillation detector may require further isolation from the defibrillation shock provided by the defibrillator 210. This increased isolation may be provided by, for example, a high pass filter having a short time constant causing the amplifier to recover quickly, an amplfier providing a dynamic range and does not saturate in respose to the application of high voltage, or passing a bias signal through the amplifier and/or electrodes before or after termination of the shock to offset the result of the shock instead of waiting for the signal to settle.

Referring again to FIG. 2A, the recorder circuit 230 records the cardiac data detected by the detector circuit 110 immediately after termination of the defibrillation shock produced by the defibrillator 110. The recorder circuit may include a plurality of recording electrodes that facilitate the recording of the influence of the first defibrillation shock on the patient. The recorder circuit 230 is also isolated from the effects of the defibrillation shock by the isolation circuit 220 as discussed above with respect to the detector circuit 110. Isolation of the recorder circuit 230 may be important to allow recording of the information detected immediately after termination of the defibrillation shock. If the circuitry of the recording circuit 230 is not isolated, the detected information may not be useful because it may be unavailable.

Finally, the controller circuit 240 may be configured to trigger alternate treatments if the detector circuit 110 reveals that the fibrillation of the heart halted immediately after termination of the defibrillation shock and/or quickly restarted. As discussed above, a patient is typically shocked at increasingly larger voltages until fibrillation halts. If the cause of the fibrillation is still present in the heart, increasing the strength of the shocks may do more harm than good. Thus, alternate treatments may be advantageous to those patients suffering from conditions that cause fibrillation to persist after halting briefly. The controller circuit 240 may be coupled to the detector circuit 110 as illustrated in FIG. 2A. The detector circuit 110 may notify the controller circuit that an alternate treatment should be administered. Once an alternate treatment is triggered, the controller circuit may automatically administer an alternate treatment or may provide a selection of alternate treatments for the healthcare provider to choose from.

In operation, according to certain embodiments of the present invention, the defibrillator 210 applies a defibrillation shock to the heart through the electrode(s). Just before the defibrillator 210 applies the defibrillation shock to the heart, the isolation circuit 220 may decouple the sensor leads of the detector circuit 110 and/or the electrodes from the defibrillator 210 to isolate the detection circuit from the high voltages produced by the defibrillation shock. The isolation circuit 220 decouples the detector circuit from the defibrillator just before administration of the defibrillation shock, during administration of the defibrillation shock and just after the termination of the defibrillation shock. For example, the sensor leads of the detector circuit 110 may be decoupled from the defibrillator 210 from about 0.3 seconds before administration of the defibrillation shock to about 0.3 seconds after the termination of the defibrillation shock.

The defibrillator 210 may notify the isolation circuit 220 when the defibrillation shock is about to be administered and when the defibrillation shock has terminated. Alternatively, the isolation circuit 220 could sense the initiation and/or termination of the defibrillation shock, be notified of the initiation of the shock and wait a predefined time period or utilize other similar techniques to determine that the defibrillation shock has terminated. Immediately after termination of the defibrillation shock, the detector circuit is able to detect cardiac function and the recorder circuit 230 is able to record cardiac function. If, for example, the detector circuit 110 detects that fibrillation has ceased immediately after the fibrillation shock, the detector circuit 110 notifies the controller circuit 240 that fibrillation has ceased immediately after termination of the fibrillation shock. The controller circuit 240 may administer an alternate therapy based on the signals detected from the detector circuit 110. The controller circuit 240 may be configured to administer the alternate therapy automatically or may wait for input from a healthcare provider. If, on the other hand, fibrillation is detected immediately after termination of the fibrillation shock, conventional therapies may be administered. Operations of the circuits illustrated in FIG. 2A will be discussed further below with respect to the flow charts of FIGS. 5 through 12 illustrating operations according to embodiments of the present invention.

Figure 3:
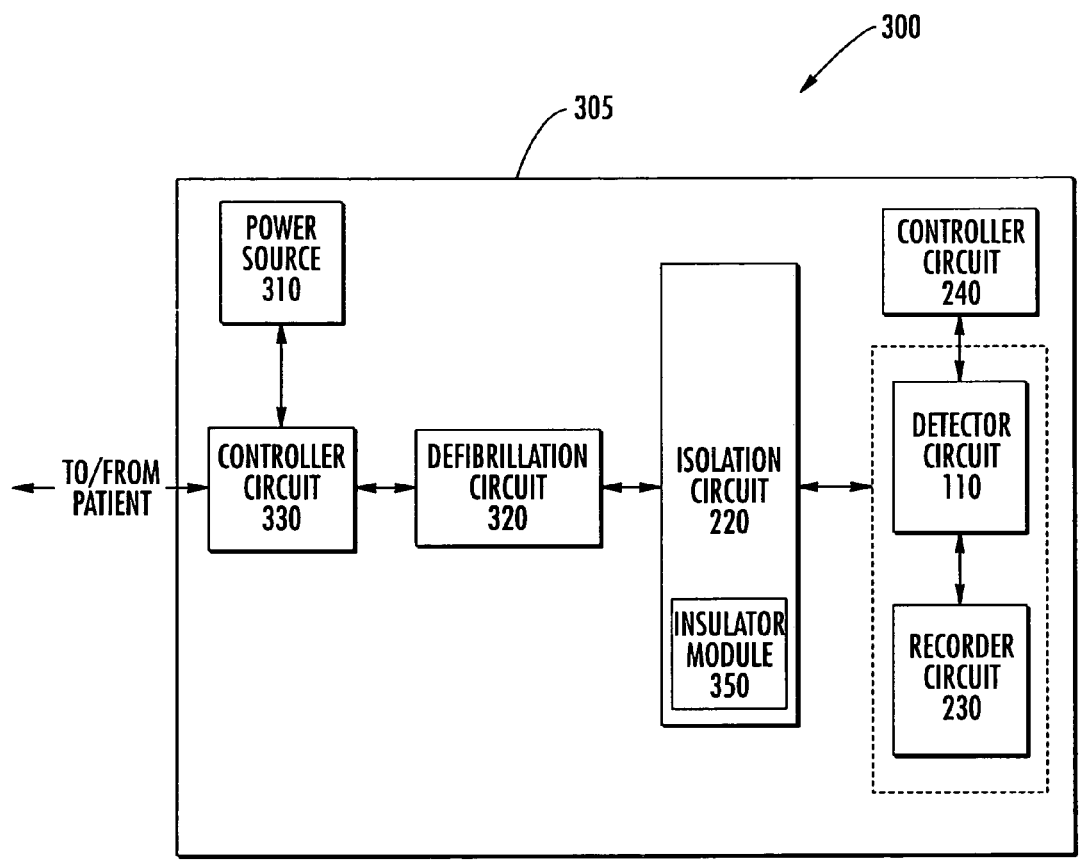
FIG. 3 is a block diagram of a defibrillator including a detector according to embodiments of the present invention.

Referring now to FIG. 3, a block diagram of a defibrillator 300 including a detector circuit 110 according to embodiments of the present invention will be discussed. The defibrillator 300 may include a housing 305. The housing may be for an implantable defibrillator or an external defibrillator. The defibrillator 300 may further include a power source 310 held in the housing 305 and a controller 330 held in the housing 305 and operatively associated with the power source 310. A defibrillation circuit 320 is held in the housing and operatively associated with the power source 310 and the controller 330. The defibrillation circuit 320 may be configured to selectively deliver a plurality of different defibrillation shocks based upon whether or not fibrillation is present in the patient immediately after termination of the first defibrillation shock. A detector circuit 110 may be operatively associated with the controller circuit for detecting the presence or absence of fibrillation in a patient immediately after termination of the defibrillation shock to the patient's heart. The results of this detection may be recorded by recorder circuit 230, which may be operably associated with the detector circuit 110. An isolation circuit 220, also operably associated with the detector circuit 110 and the recorder circuit 230, may be configured to isolate and/or decouple the detector circuit 110 from the defibrillation circuit 320 before initiation of, during and after termination of the shock delivered by the defibrillation circuit in order to allow the fibrillation detector to recover and detect/record cardiac activity in a patient immediately after termination of the defibrillation shock.

The isolation circuit 220 may further include an insulator module 350 if the defibrillator 300 is an internal defibrillator disposed within an implantable housing. As discussed above, the detector circuit 110 may require extra isolation if it is disposed within an internal defibrillator located in or around heart tissue. Furthermore, a controller circuit 340 may be operably associated with the detector circuit 110 to provide alternative treatments for fibrillation as discussed further with respect to FIGS. 5 through 12 below.

Figure 4:
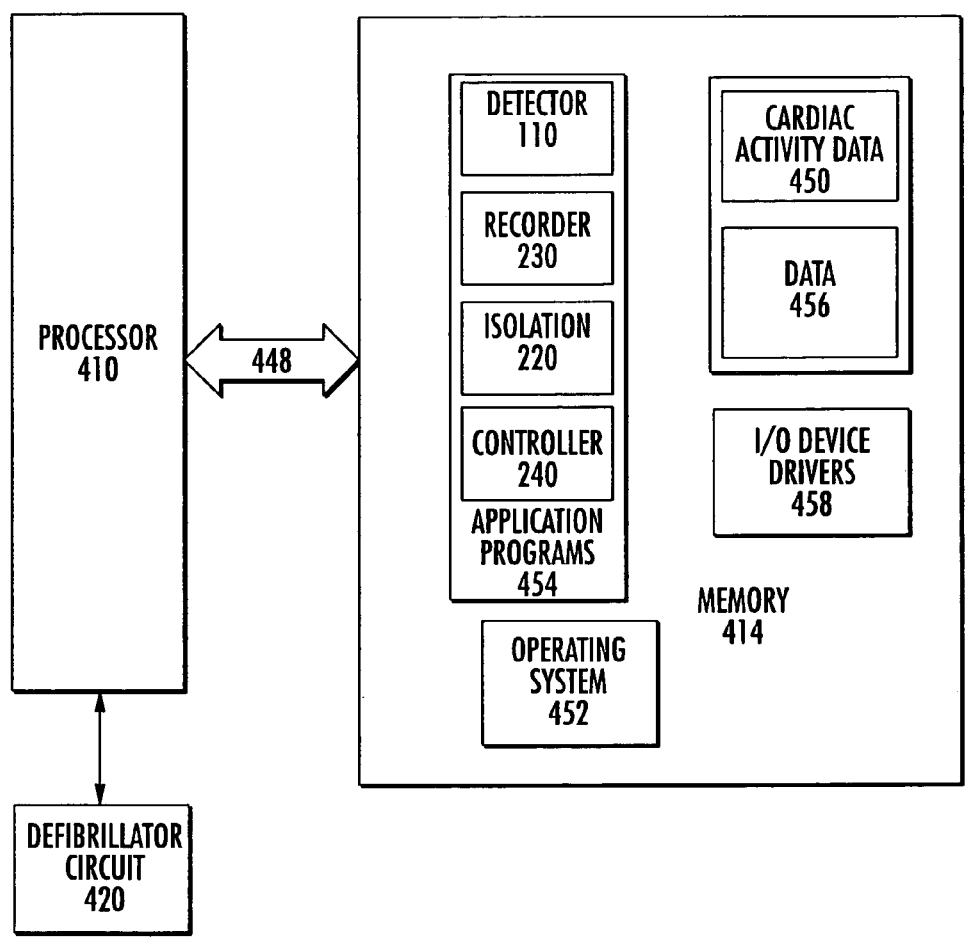
FIG. 4 is a block diagram of operational circuitry and/or computer program modules of a detector according to embodiments of the present invention.
Figure 5:
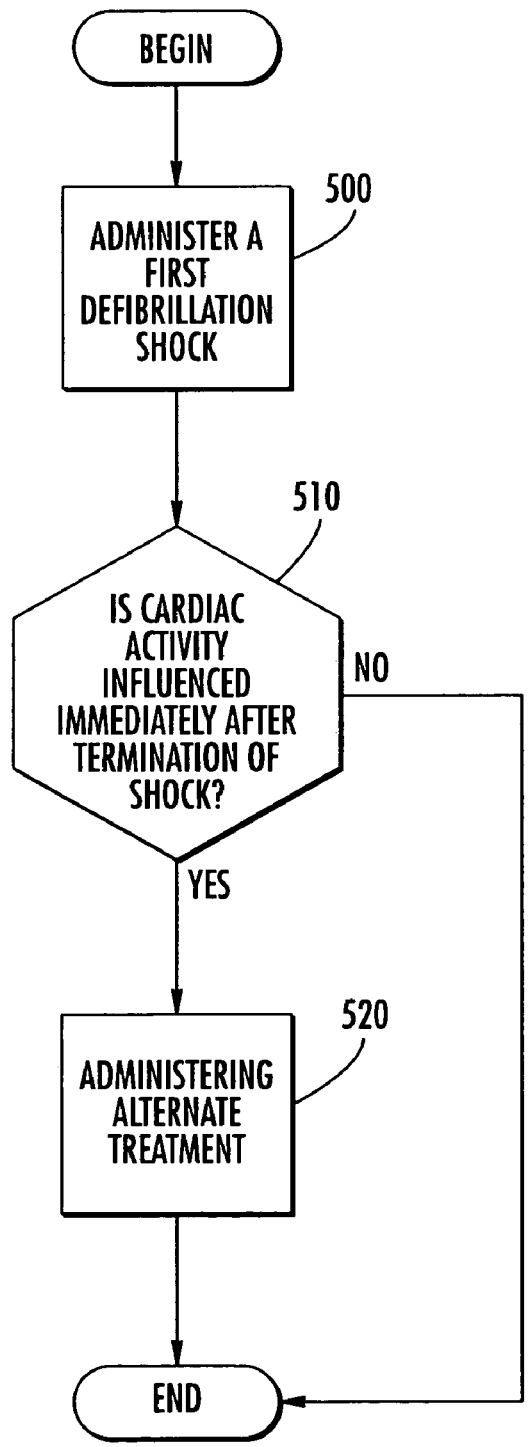
FIG. 5 is a flow chart illustrating operations of devices according to embodiments of the present invention.

Now referring to FIG. 4, a block diagram illustrating operational circuitry and/or computer program modules of a fibrillation device according to embodiments of the present invention will be discussed. FIG. 4 illustrates systems, methods, and computer program products in accordance with embodiments of the present invention. The data processing system may be implemented externally or internally with respect to the patient. The defibrillator circuit 420 may be external to the patient or implanted in the patient. If the defibrillator circuit 420 is implanted in the patient, it may include sensors either implanted in the patient along with it or situated at internal or external regions of the patient.

The processor 410 communicates with the memory 414 via an address/data bus 448. The processor 410 can be any commercially available or custom microprocessor. The memory 414 is representative of the overall hierarchy of memory devices containing the software and data used to implement the functionality of the data processing system. The memory 414 can include, but is not limited to, the following types of devices: cache, ROM, PROM, EPROM, EEPROM, flash memory, SRAM, and DRAM.

As shown in FIG. 4, the memory 414 may include several categories of software and data used in the data processing system: the operating system 452; the application programs 454; the input/output (I/O) device drivers 458; and the data 456. The data 456 may include cardiac function data 450 which may be obtained from a detector 110 and/or recorder 230. The cardiac data includes, but is not limited to electrical activity and blood pressure.

As will be appreciated by those of skill in the art, the operating system 452 may be any operating system suitable for use with a data processing system, such as OS/2, AIX, OS/390 or System390 from International Business Machines Corporation, Armonk, N.Y., Windows CE, Windows NT, Windows95, Windows98 or Windows2000 from Microsoft Corporation, Redmond, Wash., Unix or Linux or FreeBSD, Palm OS from Palm, Inc., Mac OS from Apple Computer, or proprietary operating systems. The I/O device drivers 458 typically include software routines accessed through the operating system 452 by the application programs 454 to communicate with devices such as I/O data port(s), data storage 456 and certain memory 414. The application programs 454 are illustrative of the programs that implement the various features of the data processing system and preferably include at least one application which supports operations according to embodiments of the present invention. Finally, the data 456 represents the static and dynamic data used by the application programs 454, the operating system 452, the I/O device drivers 458, and other software programs that may reside in the memory 414.

While the present invention is illustrated, for example, with reference to the detector 110, recorder 230, isolation circuit 220 and controller 240 being application programs in FIG. 4, as will be appreciated by those of skill in the art, other configurations may also be utilized while still benefiting from the teachings of the present invention. For example, the detector 110 may also be incorporated into the operating system 452, the I/O device drivers 458 or other such logical division of the data processing system. Thus, the present invention should not be construed as limited to the configuration of FIG. 4, which is intended to encompass any configuration capable of carrying out the operations described herein.

In certain embodiments, the detector 110, the recorder 230, the isolation circuit 220 and the controller 240 include computer program code for obtaining data associated with the presence of cardiac activity in the patient immediately after termination of a defibrillation shock. The I/O data port can be used to transfer information between the data processing system and the defibrillator circuit 420 or another computer system or a network (e.g., the Internet) or to other devices controlled by the processor. These components may be conventional components such as those used in many conventional data processing systems that may be configured in accordance with the present invention to operate as described herein.

While certain embodiments of the present invention are illustrated in the figures, for example, with reference to particular divisions of programs, functions and memories, the present invention should not be construed as limited to such logical divisions. Thus, the present invention should not be construed as limited to the configuration of operation as shown in FIGS. 1 through 4 but is intended to encompass any configuration capable of carrying out the operations described herein.

Embodiments of the present invention will now be further described herein with respect flow chart illustrations of operations of the present invention depicted in FIGS. 5 through 12. Now referring to FIG. 5, a flow chart illustrating operations of treating a patient according to embodiments of the present invention will be discussed. A first defibrillation shock is administered to the patient using, for example, a defibrillator as discussed above. The defibrillation shock may have a first shock value and is administered to the patient at a first time (block 500). The defibrillation shock may be administered by any defibrillation circuit know to those of skill in the art and is not limited to the defibrillators discussed above with respect to FIGS. 1 through 4. For example, the defibrillator may be atrial or ventricular, internal or external to the patient, or any combination of these as discussed above.

It is determined if cardiac activity, for example, fibrillation and/or tachycardia, in the patient has been influenced by the first defibrillation shock immediately after termination of the first defibrillation shock (block 510). This determination may be made by utilizing the detector circuit discussed above with respect to FIGS. 1 through 4. As used herein, the term "influence" may include an absence of the cardiac activity, for example, fibrillation and/or tachycardia, targeted by the defibrillation shock and/or a change in the characterization of the targeted cardiac activity. As discussed above, the term "immediately" refers to detection or application of stimulation before a conventional electro-cardiagram can detect cardiac activity to determine if the defibrillation shock successfully halted fibrillation. Thus, for example, detection of cardiac activity or application of stimulation less than about 2 to 4 seconds after the termination of the defibrillation shock may be considered immediately after termination of the defibrillation shock. In particular embodiments of the present invention, the detection and/or stimulation occurs within about 2 seconds of termination of the defibrillation shock, in further embodiments the detection and/or stimulation occurs within about 1 second of the termination of the defibrillation shock and in still further embodiments of the present invention, the detection and/or stimulation occurs within about 0.5 seconds of the termination of the defibrillation shock.

If it is determined that the first defibrillation shock did influence the fibrillation immediately after the first defibrillation shock an alternate treatment is administered at a second time (block 520). Alternate treatments may include, for example, CPR and pacing instead of increasing the strength of the defibrillation shock and reshocking the patient. The alternate treatment methods will be discussed further below with respect to FIGS. 7 through 12.

Figure 6:
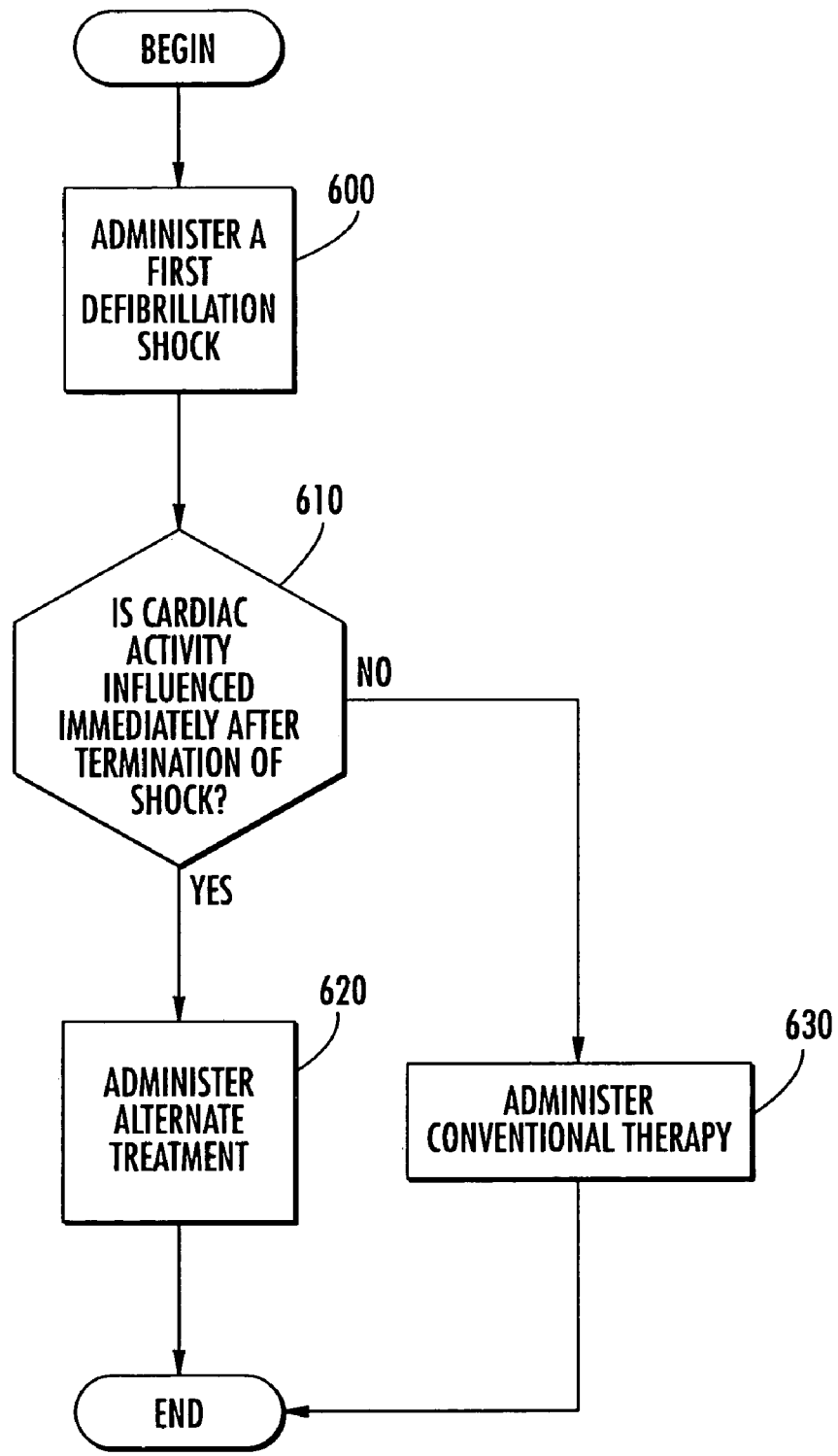
FIG. 6 is a flow chart illustrating operations of devices according to embodiments of the present invention.
Figure 7:
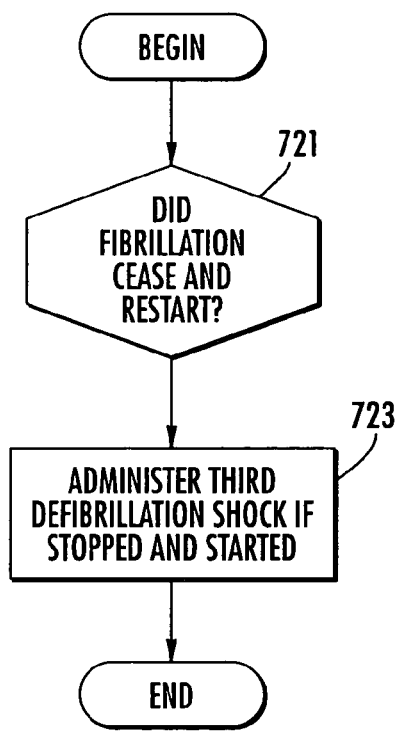
FIG. 7 is a flow chart illustrating operations of administering alternate treatment according to embodiments of the present invention.

Now referring to FIG. 6, a flow chart illustrating operations of treating a patient according to embodiments of the present invention will be discussed. A first defibrillation shock may be administered to the patient. The defibrillation shock may have a first shock value and is administered to the patient at a first time (block 600). It is determined if the fibrillation in the patient has been influenced by the first defibrillation shock immediately after termination of the first defibrillation shock (block 610). If it is determined that the first defibrillation shock did influence the fibrillation immediately after the first defibrillation shock an alternate treatment is administered at the second time (block 620). On the other hand, if it is determined that the fibrillation in the patient has not been influenced by the first defibrillation shock (block 610), a conventional treatment, such as a second defibrillation shock having a second shock value that is higher than the first shock value, is administered at a second time (block 630).

Alternate treatment methods will now be discussed with reference to FIGS. 7 through 12. Now referring to FIG. 7, a flow chart illustrating an alternate treatment method will be discussed. It is determined if the cardiac activity, for example, fibrillation, ceases after the first defibrillation shock and restarts within a predetermined time period after termination of the first defibrillation shock (block 721). This determination may be made utilizing the recorder circuit in combination with the other circuitry discussed above with respect to FIGS. 1 through 4. The predetermined time period may be from about 0 to about 5 minutes after the first defibrillation shock. If it is determined that the fibrillation ceased after the first defibrillation shock and restarted within the predetermined time period, a subsequent defibrillation shock is administered immediately after fibrillation restarts (block 723). The third shock value may be a strength that is substantially equivalent to the first shock value or may be less than the first shock value.

For example, once the detector circuit detects that the fibrillation and/or tachycardia of the heart has ceased and reinitiated it may send an indication of this condition to the controller circuit. The controller circuit may then automatically determine the course of alternate treatment or request input from the healthcare provider on, for example, a medical monitor. For example, a series of options may be presented and the healthcare provider may select one of the series of options. With respect to the alternate treatment of FIG. 7, if the subsequent shock is administered automatically, i.e. without input from the healthcare provider, the medical staff should be alerted before the shock is administered to the patient to avoid injury to those around the patient's body. For example, an audible tone or flashing light may be used to indicate to the medical staff to stand away from the patient.

It will be understood that the words first, second and so on, are used herein to distinguish one element from another and do not imply any special meaning or order. For example, the second defibrillation shock could have been termed the third defibrillation shock without departing from the teachings of the present invention.

Figure 8:
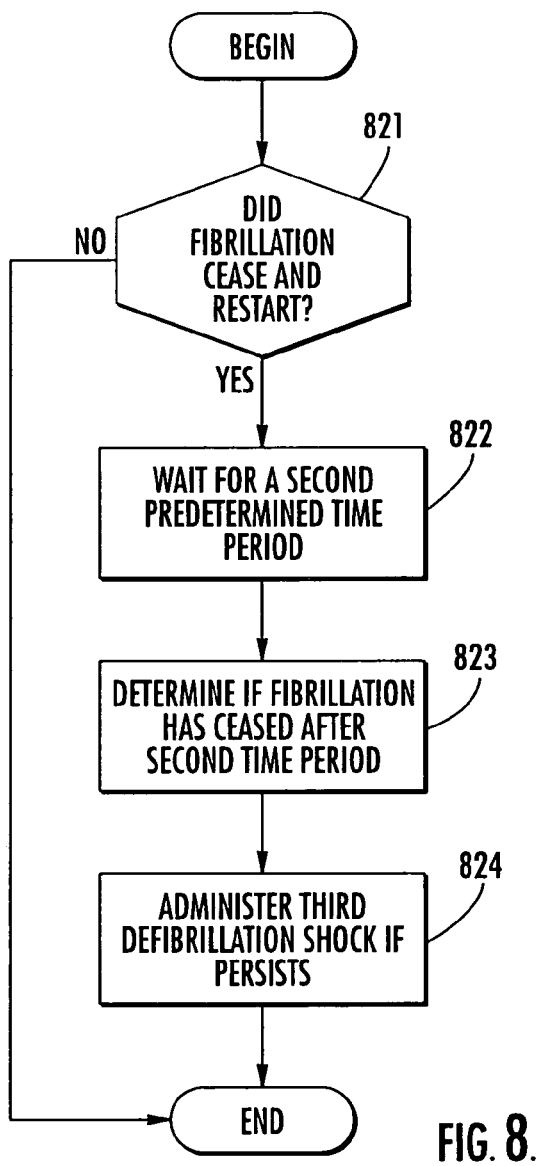
FIG. 8 is a flow chart illustrating operations of administering alternate treatment according to embodiments of the present invention.

Now referring to FIG. 8, a flow chart illustrating an alternate treatment method will be discussed. It is determined if the fibrillation ceased after the first defibrillation shock and restarted within a first predetermined time period after the first defibrillation shock (block 821). The first predetermined time period may be, for example, from about 0 to about 5 minutes after termination of the first defibrillation shock. If it is determined that the fibrillation ceased after the first defibrillation shock and restarted within the first predetermined time period, additional action is not performed for a second predetermined time period (block 822). The second predetermined time period may be from about 10 seconds to about 90 seconds. It is determined if the fibrillation ceased after the second predetermined time period (block 823). If it is determined that the fibrillation has not ceased after the second predetermined time period (block 823), a third defibrillation shock is administered having a third shock value (block 824). The third shock value may be substantially equivalent to the first shock value or less than the first shock value.

Figures 9, 10:
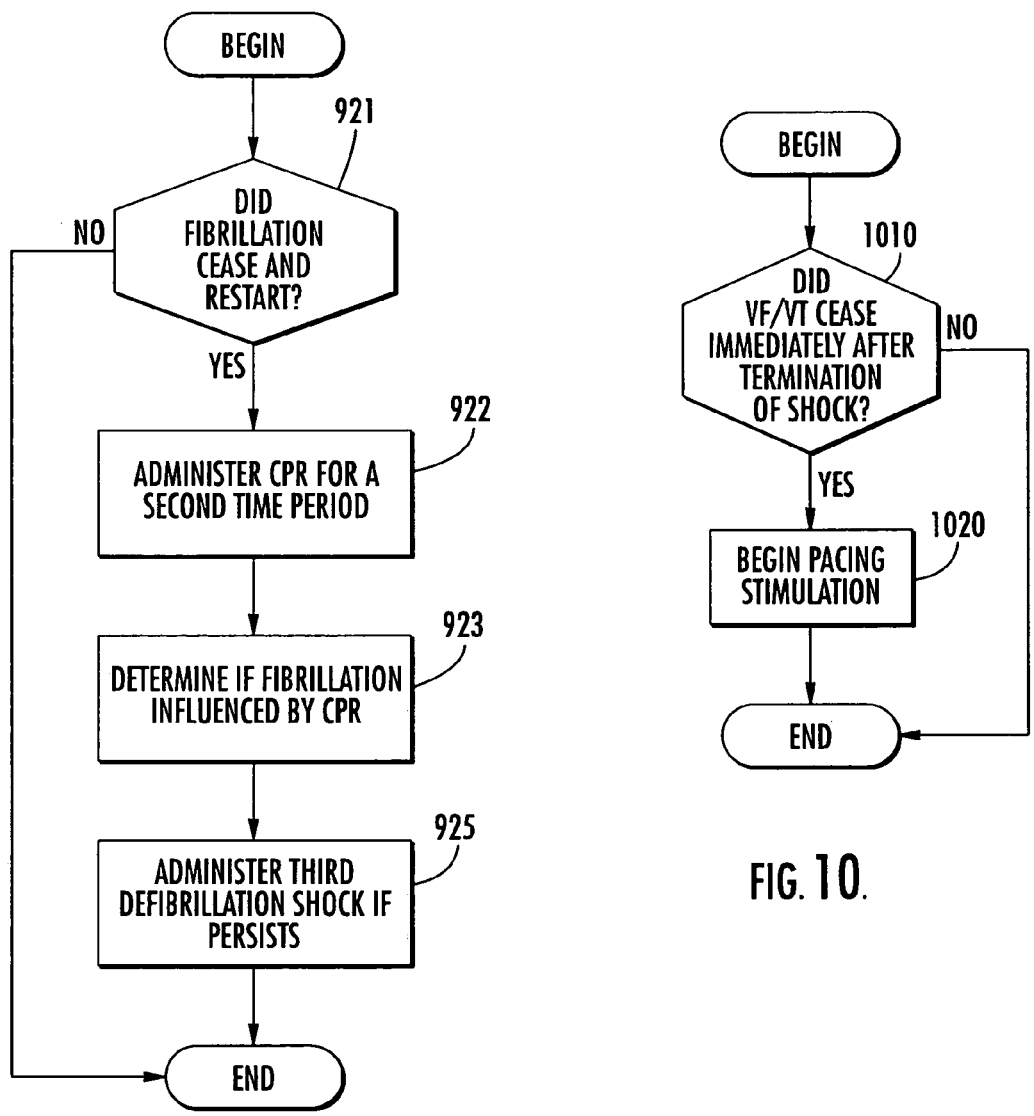
FIG. 9 is a flow chart illustrating operations of administering alternate treatment according to embodiments of the present invention.
FIG. 10 is a flow chart illustrating operations of administering alternate treatment according to embodiments of the present invention.

Now referring to FIG. 9, a flow chart illustrating an alternate treatment method will be discussed. As illustrated in FIG. 9, it is determined if the fibrillation ceased after the first defibrillation shock and restarted within a first predetermined time period after the first defibrillation shock (block 921). The first predetermined time period may be, for example, from about 0 to about 5 minutes after termination of the first defibrillation shock. If the fibrillation ceased after the first defibrillation shock and restarted within the first predetermined time period, CPR is administered for a second predetermined time period (block 922). CPR may be administered in any way known to those skilled in the art. For example, conventional CPR or CPR using a vest to perform chest compressions may be performed. The second predetermined time period may be from about 10 seconds to about 90 seconds.

It is determined if the fibrillation is influenced by the CPR after the second predetermined time period (block 923). If the fibrillation has not been influence by CPR after the second predetermined time period (i.e. the fibrillation has not stopped), a third defibrillation shock is administered (block 925). The third shock value may be substantially equivalent to the first shock value or less than the first shock value after the second predetermined time period.

Now referring to FIG. 10, a flow chart illustrating an alternate treatment method will be discussed. As seen in FIG. 10, it is determined if fibrillation has ceased after termination of the first defibrillation shock that is applied to the heart (block 1010), for example, by a defibrillator. If it is determined that fibrillation has ceased, pacing stimulation is applied to the heart (block 1020) by, for example, the controller circuit discussed above with respect to FIGS. 1 through 4. If, on the other hand, it is determined that fibrillation has not ceased (block 1010), conventional methods of treatment may be administered. As discussed above, termination of the defibrillation shock may be determined, for example, by the defibrillator circuit notifying the controller circuit of termination of the shock or the controller circuit detecting termination of the shock.

Although the present invention is discussed above with respect to ventricular fibrillation (VF), embodiments of the present invention are not limited to this condition. For example, it may be determined if ventricular tachycardia (VT) has ceased and if so, then a pacing stimulation may be applied without departing from the teachings of the present invention. VT is a condition that includes an abnormally fast heartbeat, for example, greater than 100 beats per minute.

It will be understood by those of skill in the art that the term "pacing stimulation" according to embodiments of the present invention is intended to include a pacing method having any cycle length or combination of cycle lengths. For example, pacing may include single pacing, paired pacing or any combination of the two. The pacing stimulation may be provided to reduce the likelihood of redevelopment of arrhythmia and/or to improve mechanical function of the heart. Furthermore, the timing of pacing stimulation may be controlled by feedback such as described in U.S. patent application Ser. No. 10/210,587 filed Jul. 31, 2002 and entitled Pacing Methods and Devices Using Feedback Controlled Timing, the disclosure of which is incorporated herein by reference as if set forth fully herein.

For single pacing, the pacing stimulation may be applied utilizing conventional timing relationships. Furthermore, conventional paired pacing may also be utilized according to certain embodiments of the present invention. For example, the timing between each pair of stimulation pulses may be constant and the timing between pulses within a pair may be constant. The pacing rate for single and/or paired pacing may be predefined or may be based on sensed variable, including cardiac electrical activity before or after the defibrillation shock as is known to those of skill in the art. The strength of the pacing stimulus may be predefined or may be dynamically established utilizing autocapture techniques known to those of skill in the art. Paired pacing could also be selectively utilized based on operator specification and/or sensed variables, such as pulse pressure lower than a predefined value, heat rate, timing and/or morphology of at least one intrinsic ventricular beat, changes in impedance, changes in distance and/or displacement and/or the rate of change of distance between two locations, and/or motion of a location associated with the heart. Electrode locations as described above may be utilized for single and/or paired pacing.

It will be further understood that the pacing method may be chosen based on a patient's historical response to past treatment. For example, a particular patient may not respond well to single pacing, therefore, paired pacing may always be used on this patient regardless of any outside variables.

Figure 11:
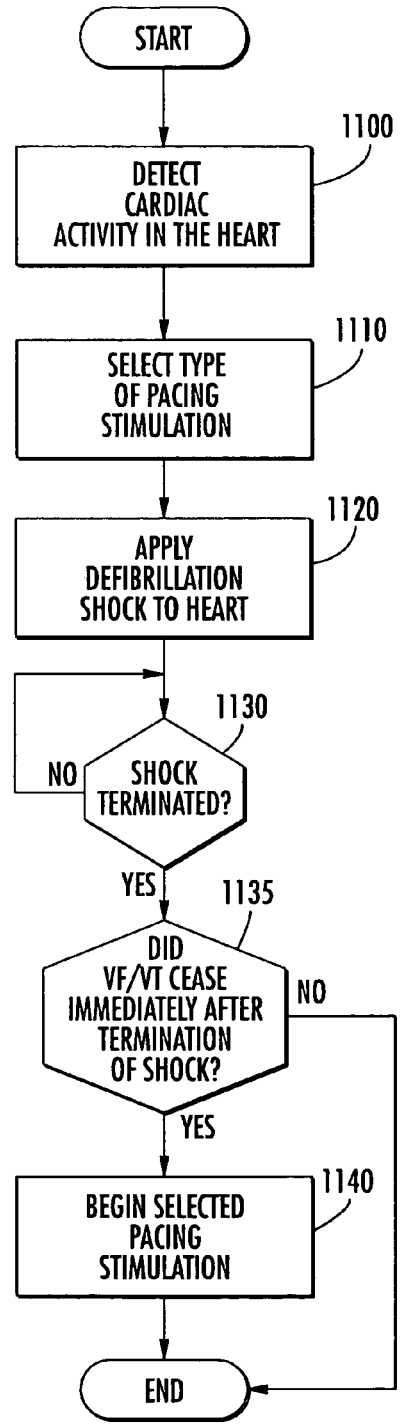
FIG. 11 is a flow chart illustrating operations of administering alternate treatment according to embodiments of the present invention.

FIG. 11 is a flowchart illustrating operations according to further embodiments of the present invention. As seen in FIG. 11, cardiac activity and/or function is detected in the heart (block 1100). Although the detection of cardiac activity and/or function is illustrated as occurring before application of the defibrillation shock in FIG. 11, the present invention is not limited to this configuration. For example, cardiac activity may be detected after the application of the defibrillation shock without departing from the teachings of the present invention. A type of pacing stimulation is selected based on the detected cardiac activity and/or function (block 1110). For example, a series of detected electrical signals (cardiac activity) may indicate that the patient would not respond to single pacing stimulation, therefore, paired pacing stimulation may be selected for this patient based upon the electrical signals. Similarly, a low pulse pressure may indicate impaired cardiac function, which may be improved by paired pacing. The type of pacing stimulation selected may include single pacing stimulation, paired pacing stimulation and/or a combination of the two.

The defibrillation shock is applied to the heart (block 1120), for example, by the defibrillator circuit. Termination of the defibrillation shock is determined (block 1130), for example, by the defibrillator circuit notifying the pacing controller circuit of termination of the shock, the pacing controller circuit detecting termination of the shock or the pacing controller circuit waiting a sufficient time to assure that the defibrillation shock has terminated. After termination of the defibrillation shock (block 1130), it is determined if the fibrillation (or VT) has ceased immediately after termination of the shock (block 1135). If fibrillation (or VT) has ceased, the selected pacing stimulation (block 1110) is applied to the heart (block 1140).

Figure 12:
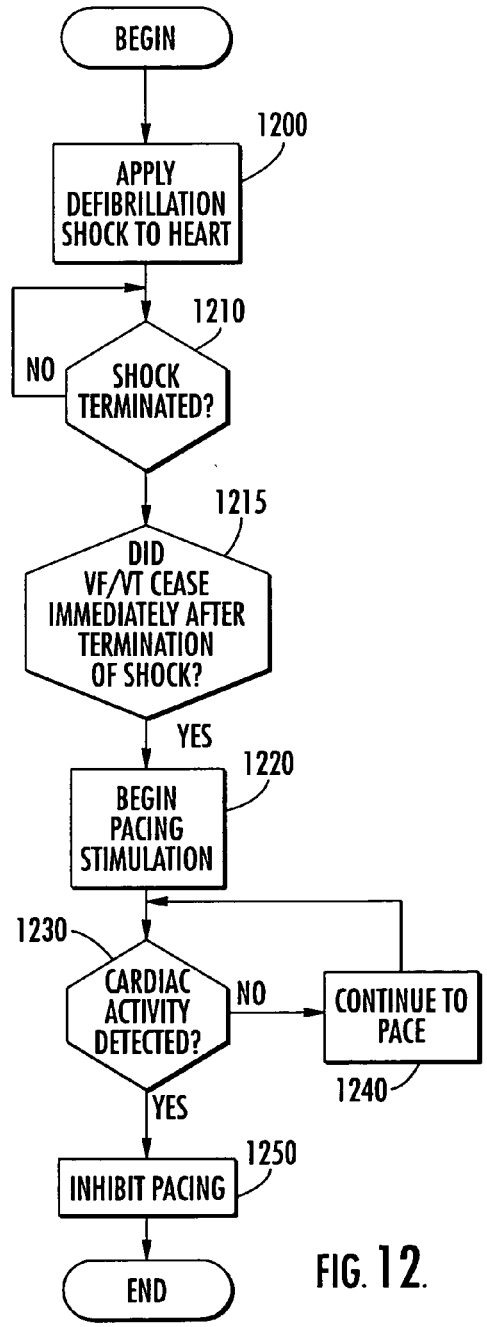
FIG. 12 is a flow chart illustrating operations of administering alternate treatment according to embodiments of the present invention.

FIG. 12 is a flowchart illustrating operations according to further embodiments of the present invention. As seen in FIG. 12, a defibrillation shock is applied to the heart (block 1200). Termination of the defibrillation shock is determined (block 1210). After termination of the defibrillation shock (block 1210), it is determined if fibrillation (or VT) has ceased immediately after termination of the defibrillation shock (block 1215). If it is determined that fibrillation has ceased immediately after the termination of the fibrillation shock (block 1215), pacing stimulation is applied to the heart (block 1220). It is determined if cardiac activity is present (block 1230). Cardiac activity may be detected by detecting, for example, blood pressure, spontaneous electrical activity or the like. If it is determined that cardiac activity is present (block 1230), pacing is inhibited (block 1250). Pacing may be inhibited by, for example, halting pacing and/or pacing less frequently. If, on the other hand, it is determined that cardiac activity is not present (block 1230), pacing continues uninterrupted (block 1240).

Figure 13:
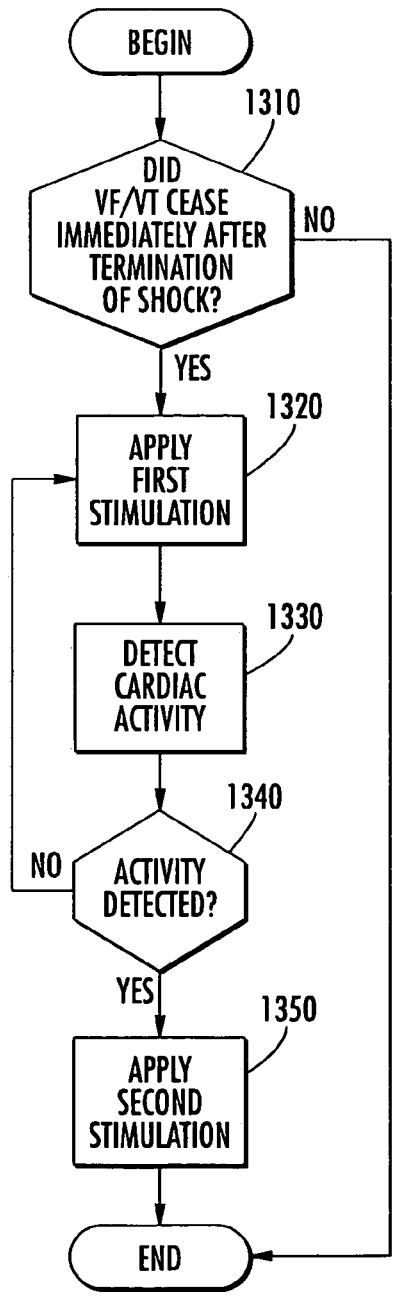
FIG. 13 is a flow chart illustrating operations of administering alternate treatment according to embodiments of the present invention.

An embodiment of the present invention utilizing paired pacing will be discussed with respect to FIG. 13. As illustrated in FIG. 13, it is determined if fibrillation has ceased immediately upon termination of the defibrillation shock (block 1310). If it is determined that defibrillation has ceased, a first pacing stimulation signal is applied to the heart (block 1320). Activity of the heart is detected that results from the application of the first pacing stimulation signal (block 1330). Based on detected cardiac activity associated with or responsive to the application of the first stimulation signal (block 1330), a second stimulation signal is selectively applied to the heart (block 1350) so as to selectively provide paired pacing based on the detected cardiac activity. The selective application of the second stimulation signal to provide paired pacing may be based on the nature of the sensed cardiac activity. Thus, if the detected cardiac activity is indicative of low cardiac function, the second stimulation signal may be applied so as to provide paired pacing to improve mechanical function of the heart. For example, the sensed cardiac function may include sensing low pulse pressure impedance signals, heat rate, timing and/or morphology of at least one intrinsic ventricular beat, changes in impedance, changes in distance and/or displacement and/or the rate of change of distance between two locations, and/or motion of a location associated with the heart. Thus, according to the embodiments illustrated in FIG. 13, the second stimulus is provided to provide paired pacing based on cardiac activity corresponding to the first stimulus (single pacing).

In further embodiments of the present invention, paired pacing may be initiated by receipt of a signal from an external source, such as a healthcare professional, that may be utilized to selectively activate paired pacing. In such a case, the operations of FIG. 14 could be modified by modifying block 1420 to determine if the signal from the external source is detected. If so, the second stimulation of block 1450 would be provided. In an implantable device, the signal from an external source may be a radio frequency signal or other such technique for communicating with an implantable device. Similarly, a software switch may be set to provide the signal from an external source. In an external device, a switch setting (either hardware or software) may be utilized to select between single pacing and paired pacing.

In still further embodiments of the present invention, the detected cardiac activity need not be responsive to the application of the first stimulation signal. In such embodiments, FIG. 13 could be modified such that activity of the heart is detected irrespective of whether the activity results from application of the first stimulation signal (block 1320). Based on the detected cardiac activity (block 1330), a second stimulation signal is selectively applied to the heart (block 1350) so as to selectively provide paired pacing based on the detected cardiac activity.

Figure 14:
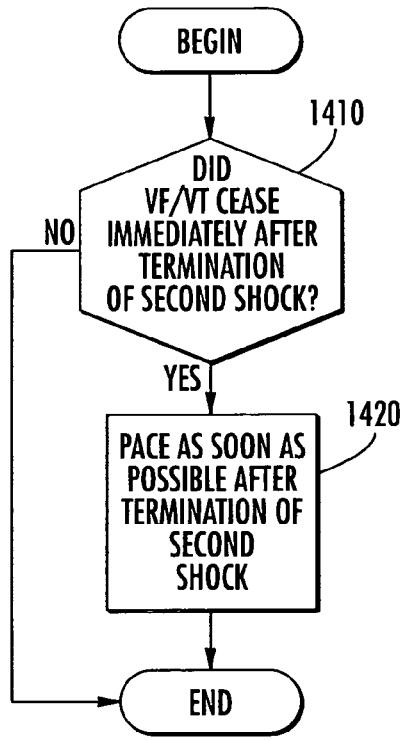
FIG. 14 is a flow chart illustrating operations of administering alternate treatment according to embodiments of the present invention.

Now referring to FIG. 14, a flow chart illustrating an alternate treatment method will be discussed. It is determined if fibrillation has ceased after the second defibrillation shock (block 1410). If it is determined that fibrillation has ceased after the second defibrillation shock, pacing will begin as soon as possible after the termination of second defibrillation shock (block 1410). Pacing in this embodiment may use any of the pacing methods discussed above.

As discussed herein with respect to FIGS. 1 through 14, a detector circuit according to embodiments of the present invention can detect cardiac activity immediately after termination of the defibrillation shock. This detection makes it possible to provide new methods of treating fibrillation that may be better tailored to a patients condition.

As will be appreciated by one of skill in the art, the present invention may be embodied as a method, data processing system, or computer program product. Accordingly, the present invention may take the form of an entirely hardware embodiment, an entirely software embodiment or an embodiment combining software and hardware aspects, all generally referred to herein as a "circuit." Furthermore, the present invention may take the form of a computer program product on a computer-usable storage medium having computer-usable program code means embodied in the medium. Any suitable computer readable medium may be utilized including, a memory device, hard disks, CD-ROMs, optical storage devices, a transmission media, such as a wireless transmission media and/or those supporting the Internet or an intranet, or magnetic storage devices.

The present invention is described herein with reference to flowchart illustrations and/or block and/or flow diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions specified in the flowchart and/or block and/or flow diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart and/or block diagram block or blocks.

While embodiments of the present invention have been described with reference to a particular architecture and/or division of functions, the present invention should not be construed as limited to such architecture and/or division. Thus, other architectures and/or division of functions capable of carrying out the operations described herein may be utilized while still falling within the teachings of the present invention. Furthermore, while embodiments of the present invention have been described with reference to particular circuits, such circuits may include discrete components, processors, such as a microprocessor and/or signal processor, analog circuits, digital circuits and/or combinations thereof. Furthermore, embodiments of the present invention may be provided as an entirely hardware embodiment, an entirely software embodiment or combinations of hardware and software.

With regard to the operations illustrated in the flowcharts described above, as will be appreciated by those of skill in the art in light of the present disclosure, embodiments of the present invention are not limited to the specific sequence or sequences of operations described therein. Thus, for example, operations in the flowcharts may be provided out of sequence or concurrently. Similarly, other sequences of operations may be utilized while still providing the feedback adjustment according to embodiments of the present invention. Accordingly, the present invention should not be construed as limited to the particular operations or sequence of operations illustrated in the flowcharts.

The foregoing is illustrative of the present invention and is not to be construed as limiting thereof Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A device for detecting the presence of cardiac activity in a patient, comprising:
   a detector circuit that is configured to detect the influence of a first defibrillation shock on the patient immediately subsequent to termination of a first defibrillation shock;
   an isolation circuit configured to electrically isolate the detector circuit from the first defibrillation shock, wherein the detected cardiac activity comprises fibrillation and wherein the detector circuit is further configured to detect if the fibrillation ceases immediately after termination of the first defibrillation shock and reinitiates within a predetermined time period after the first defibrillation shock; and
   a controller circuit wherein the controller circuit is configured to administer a second defibrillation shock having a second shock value that is at least one of substantially equivalent to the first shock value and less than the first shock value immediately if it is determined that the fibrillation has ceased immediately after termination of the first defibrillation shock and reinitiated within the predetermined time period.

2. A device according to claim 1, wherein the detector circuit is further configured to detect the influence of the first defibrillation shock on the patient within about two seconds of termination of the first defibrillation shock.

3. A device according to claim 1, wherein the device further comprises a defibrillator circuit configured to administer the first defibrillation shock to the patient.

4. A device according to claim 3, wherein the device further comprises a recorder circuit configured to record the influence of the first defibrillation shock on the patient immediately subsequent to termination of the first defibrillation shock.

5. A device according to claim 4, wherein the recorder circuit is further configured to record the influence of the first defibrillation shock on the patient within about two seconds of termination of the first defibrillation shock.

6. A device according to claim 4, wherein the isolation circuit is further configured to electrically isolate the detector circuit from the defibrillation shock from about 0.3 seconds before initiation of the first defibrillation shock to about 0.3 seconds after termination of the first defibrillation shock.

7. A device according to claim 4, wherein the isolation circuit comprises at least one of a relay and a switch.

8. A device according to claim 4, wherein the defibrillator circuit comprises a plurality of electrodes and wherein the isolation circuit is further configured to decouple the plurality of electrodes of the defibrillator circuit from the detector circuit before initiation of the first defibrillation shock until after termination of the first defibrillation shock.

9. A device according to claim 4, wherein the isolation circuit is further configured to decouple the plurality of electrodes of the defibrillator circuit from the recorder circuit before initiation of the first defibrillation shock until after termination of the first defibrillation shock.

10. A device according to claim 4, wherein the detector circuit comprises at least one amplifier and wherein the isolation circuit is further configured to decouple the at least one amplifier from the defibrillation circuit.

11. A device according to claim 4, wherein the detector circuit comprises at least one amplifier and wherein the isolation circuit is further configured to decouple the at least one amplifier by isolating at least one sensor lead from the detector circuit.

12. A device according to claim 4, wherein the isolation circuit is further configured to pass a current through the detector circuit.

13. A device according to claim 4, wherein the detector circuit further comprises at least one amplifier configured to have a large dynamic range associated therewith.

14. A device according to claim 4, wherein the detector circuit, the defibrillator circuit, the recorder circuit and the isolation circuit are configured to be disposed within a single implantable housing for implantation in the patient.

15. A device according to claim 14, wherein the implantable housing is an implantable defibrillator.

16. A device according to claim 15, wherein the isolation circuit further comprises an insulator module that is configured to insulate the detector circuit within the implantable defibrillator from the first defibrillation shock.

17. A device according to claim 4, where the detector circuit, the defibrillator circuit, the recorder circuit and the isolation circuit are configured to be disposed within a single housing that is external to the patient.

18. A device according to claim 17, wherein the single housing is an external defibrillator.

19. A device according to claim 4, wherein the detector circuit, the defibrillator circuit, the recorder circuit and the isolation circuit are respective separate devices.

20. A device according to claim 19, wherein at least one of the detector circuit, the defibrillator circuit, the recorder circuit and the isolation circuit is configured to be disposed within an implantable housing for implantation within the patient and at least one of the detector circuit, the defibrillator circuit, the recorder circuit and the isolation circuit is configured to be external to the patient.

21. A device according to claim 4, wherein the defibrillator circuit is further configured to indicate termination of the defibrillation shock to the detector circuit.

22. A device according to claim 1, wherein the detector circuit is further configured to determine if the cardiac activity of the patient immediately subsequent to termination of a first defibrillation shock is normal cardiac activity.

23. A device according to claim 22, wherein the device further comprises a controller circuit configured to apply a pacing stimulation signal to a heart of a patient if the detector circuit determines that the cardiac activity of the patient immediately subsequent to termination of the first defibrillation shock is normal cardiac activity.

24. A device according to claim 23, wherein the controller circuit is further configured to apply the pacing stimulation within about two seconds of termination of the defibrillation shock.

25. A device according to claim 23, wherein the pacing stimulation signal comprises single pacing stimulation.

26. A device according to claim 25, wherein the controller circuit is further configured to detect cardiac activity of the heart associated with application of the single pacing stimulation and selectively apply paired pacing stimulation based on the detected cardiac activity.

27. A device according to claim 25, wherein the controller circuit is further configured to detect cardiac activity of the heart and selectively apply paired pacing stimulation based on the detected cardiac activity.

28. A device according to claim 23, wherein the pacing stimulation signal comprises paired pacing stimulation.

29. A device according to claim 23, wherein the controller circuit is further configured to detect a signal specifying application of paired pacing and selectively apply paired pacing stimulation based on the detected signal.

30. A device according to claim 23, wherein the defibrillation shock is applied to a heart of a patient using at least one first set of electrodes and wherein the controller circuit is further configured to apply the pacing stimulation signal to the heart of the patient subsequent to termination of the defibrillation shock using at least one second set of electrodes, wherein the first set of electrodes and the second set of electrodes are different sets of electrodes.

31. A device according to claim 23, wherein the defibrillation shock is applied to a heart of a patient using at least one first set of electrodes and wherein the controller circuit is further configured to apply the pacing stimulation signal to the heart of the patient subsequent to termination of the defibrillation shock using at least one second set of electrodes, wherein the first set of electrodes and the second set of electrodes are the same set of electrodes.

32. A device according to claim 23, wherein the controller circuit is further configured to selectively apply paired pacing stimulation to the heart based on at least one of receipt of an external specification and sensed variables associated with cardiac activity.

33. A device according to claim 32, wherein the sensed variables associated with cardiac activity comprise a pulse pressure below a predefined threshold.

34. A device according to claim 33, wherein the controller circuit is configured to be disposed within an implantable housing for implantation in the patient.

35. A device according to claim 32, wherein the external specification comprises instruction from a healthcare provider.

36. A device according to claim 23, wherein the controller circuit is configured to be external to the patient.

37. A device according to claim 23, further comprising at least one set of electrodes for application of the pacing stimulation signal to the heart of the patient.

38. A device according to claim 24, wherein the controller circuit is further configured to apply the pacing stimulation within about one second of termination of the defibrillation shock.

39. A device according to claim 1, further comprising a controller circuit wherein the controller circuit is configured to:
wait a second predetermined time period if it is determined that the fibrillation ceased immediately after termination of the first defibrillation shock and reinitiated within the first predetermined time period; and
determine if fibrillation ceases after termination of the second predetermined time period; and
administer a third defibrillation shock having a third shock value that is at least one of substantially equivalent to the first shock value and less than the first shock value after the second predetermined time period if it is determined that the fibrillation has not ceased after termination of the second predetermined time period.

40. A device according to claim 1, further comprising a controller circuit wherein the controller circuit is configured to:
   administer cardiopulmonary resuscitation (CPR) for a second predetermined time period if the fibrillation ceased immediately after termination of the first defibrillation shock and reinitiated within the first predetermined time period;
   determine if the cardiac activity has been influenced by the administration of CPR; and
   administer a third defibrillation shock having a third shock value that is at least one of substantially equivalent to the first shock value and less than the first shock value after termination of the second predetermined time period if it is determined that the fibrillation activity has not been influenced by the administration of CPR during the second predetermined time period.

41. A device according to claim 1, further comprising a controller circuit wherein the controller circuit is configured to:
   administer a second defibrillation shock having a second shock value that is higher than the first shock value at the second time if the fibrillation is not influenced by the first defibrillation shock immediately after termination of the first defibrillation shock.

42. A device according to claim 23:
   wherein the controller circuit is further configured to detect cardiac activity and/or function of the heart, select a type of pacing stimulation to apply to the heart of the patient subsequent to termination of the defibrillation shock based on the detected cardiac activity and/or function and apply the selected type of pacing stimulation.

43. A device according to claim 42, wherein the controller circuit is further configured to detect the cardiac activity and/or function before applying a defibrillation shock to a heart of the patient.

44. A device according to claim 42, wherein the controller circuit is further configured to detect the cardiac activity and/or function after applying a defibrillation shock to a heart of the patient.

45. A device according to claim 42, wherein the selected type of pacing stimulation comprises single pacing stimulation.

46. A device according to claim 42, wherein the selected type of pacing stimulation comprises paired pacing stimulation.

47. A device according to claim 42, wherein the selected type of pacing stimulation comprises a combination of single pacing stimulation and paired pacing stimulation.

48. A device according to claim 23, wherein the controller circuit is further configured to inhibit application of the pacing stimulation if cardiac activity is detected.

49. A device according to claim 48, wherein the detected cardiac activity comprises a detected blood pressure.

50. A device according to claim 48, wherein the detected cardiac activity comprises spontaneous electrical activity.

51. A system for detecting the presence of cardiac activity in a patient, comprising:
   a first set of electrodes for applying a first defibrillation shock to a heart of the patient;
   means for detecting the influence of the first defibrillation shock on the patient immediately subsequent to termination of a first defibrillation shock;
   means for electrically isolating the means for detecting from the means for administering, wherein the detected cardiac activity comprises fibrillation and wherein the means for detecting comprises means for detecting if the fibrillation ceases immediately after termination of the first defibrillation shock and reinitiates within a predetermined time period after the first defibrillation shock; and
   means for administering a second defibrillation shock having a second shock value that is at least one of substantially equivalent to the first shock value and less than the first shock value immediately if it is determined that the fibrillation has ceased after termination of the first defibrillation shock and reinitiated within the predetermined time period.

52. A system according to claim 51, wherein the means for detecting further comprises detecting the influence of the first defibrillation shock on the patient within about two seconds of termination of the first defibrillation shock.

53. A system according to claim 51, wherein the system further comprises means for administering the first defibrillation shock to the patient.

54. A system according to claim 53, wherein the system further comprises means for recording the influence of the first defibrillation shock on the patient immediately subsequent to termination of the first defibrillation shock.

55. A system according to claim 54, wherein the means for recording comprises means for recording the influence of the first defibrillation shock on the patient within about two seconds of termination of the first defibrillation shock.

56. A system according to claim 54, wherein the means for detecting further comprises means for determining if the cardiac activity of the patient immediately subsequent to termination of a first defibrillation shock is normal cardiac activity.

57. A system according to claim 54, wherein the system further comprises means for applying a pacing stimulation signal to a heart of a patient if the detector circuit determines that the cardiac activity of the patient immediately subsequent to termination of the first defibrillation shock is normal cardiac activity.

58. A system according to claim 57, wherein the means for applying pacing stimulation comprises means for applying the pacing stimulation within about two seconds of termination of the defibrillation shock.

59. A system according to claim 57, wherein the pacing stimulation signal comprises single pacing stimulation.

60. A system according to claim 59, wherein means for applying pacing stimulation comprises means for detecting cardiac activity of the heart associated with application of the single pacing stimulation and selectively apply paired pacing stimulation based on the detected cardiac activity.

61. A system according to claim 59, wherein the means for applying stimulation further comprises detecting cardiac activity of the heart and selectively applying paired pacing stimulation based on the detected cardiac activity.

62. A system according to claim 57, wherein the pacing stimulation signal comprises paired pacing stimulation.

63. A system according to claim 57, wherein the means for applying stimulation further comprises means for detecting a signal specifying application of paired pacing and selectively apply paired pacing stimulation based on the detected signal.

64. A system according to claim 57, wherein the defibrillation shock is applied to a heart of a patient using at least one first set of electrodes and wherein the means for applying further comprises means for applying the pacing stimulation signal to the heart of the patient subsequent to termination of the defibrillation shock using at least one second set of electrodes, wherein the first set of electrodes and the second set of electrodes are different sets of electrodes.

65. A system according to claim 57, wherein the defibrillation shock is applied to a heart of a patient using at least one first set of electrodes and wherein the means for applying further comprises means for applying the pacing stimulation signal to the heart of the patient subsequent to termination of the defibrillation shock using at least one second set of electrodes, wherein the first set of electrodes and the second set of electrodes are the same set of electrodes.

66. A system according to claim 57, wherein the means for applying further comprises means for selectively applying paired pacing stimulation to the heart based on at least one of receipt of an external specification and sensed variables associated with cardiac activity.

67. A system according to claim 57, wherein the sensed variables associated with cardiac activity comprise a pulse pressure below a predefined threshold.

68. A system according to claim 57, wherein the external specification comprises instruction from a healthcare provider.

69. A system according to claim 57, wherein the controller circuit is configured to be disposed within an implantable housing for implantation in the patient.

70. A system according to claim 57, wherein the system further comprises:
   means for detecting cardiac activity and/or function of the heart; and
   means for selecting a type of pacing stimulation to apply to the heart of the patient subsequent to termination of the defibrillation shock based on the detected cardiac activity and/or function, wherein the means for applying comprises means for applying the selected type of pacing.

71. A system according to claim 70, wherein the means for detecting further comprises means for detecting cardiac activity and/or function before administering a defibrillation shock to a heart of the patient.

72. A system according to claim 70, wherein the means for detecting further comprises means for detecting cardiac activity and/or function after administering a defibrillation shock to a heart of the patient.

73. A system according to claim 70, wherein the selected type of pacing stimulation comprises single pacing stimulation.

74. A system according to claim 70, wherein the selected type of pacing stimulation comprises paired pacing stimulation.

75. A system according to claim 70, wherein the selected type of pacing stimulation comprises a combination of single pacing stimulation and paired pacing stimulation.

76. A system according to claim 57, wherein the means for applying further comprises means for inhibiting application of the pacing stimulation if cardiac activity is detected.

77. A system according to claim 76, wherein the detected cardiac activity comprises a detected blood pressure.

78. A system according to claim 76, wherein the detected cardiac activity comprises spontaneous electrical activity.

79. A system according to claim 51, further comprising:
   means for waiting a second predetermined time period if it is determined that the fibrillation ceased after termination of the first defibrillation shock and reinitiated within the first predetermined time period; and
   means for determining if fibrillation ceases after termination of the second predetermined time period; and
   means for administering a third defibrillation shock having a third shock value that is at least one of substantially equivalent to the first shock value and less than the first shock value after the second predetermined time period if it is determined that the fibrillation has not ceased after termination of the second predetermined time period.

80. A system according to claim 51, further comprising:
   means for administering cardiopulmonary resuscitation (CPR) for a second predetermined time period if the fibrillation ceased after termination of the first defibrillation shock and reinitiated within the first predetermined time period;
   means for determining if the cardiac activity has been influenced by the administration of CPR; and
   means for administering a third defibrillation shock having a third shock value that is at least one of substantially equivalent to the first shock value and less than the first shock value after termination of the second predetermined time period if it is determined that the fibrillation activity has not been influenced by the administration of CPR during the second predetermined time period.

81. A system according to claim 51, further comprising:
   means for administering a second defibrillation shock having a second shock value that is higher than the first shock value at the second time if the fibrillation is not influenced by the first defibrillation shock immediately after termination of the first defibrillation shock.

82. A system for detecting the presence of cardiac activity in a patient, comprising:
   a defibrillator circuit configured to administer the first defibrillation shock to the patient;
   a detector circuit configured to detect the influence of the first defibrillation shock on the patient subsequent to termination of a first defibrillation shock; and
   an isolation circuit configured to electrically isolate the detector circuit from the defibrillator circuit, wherein the detected cardiac activity comprises fibrillation and wherein the detector circuit is further configured to detect if the fibrillation ceases immediately after termination of the first defibrillation shock and reinitiates within a predetermined time period after the first defibrillation shock and wherein the defibrillator circuit is further configured to administer a second defibrillation shock having a second shock value that is at least one of substantially equivalent to the first shock value and less than the first shock value immediately if it is determined that the fibrillation has ceased after termination of the first defibrillation shock and reinitiated within the predetermined time period.

83. A computer program product for detecting the presence of cardiac activity in a patient, comprising:
   computer readable medium having computer readable program code embodied therein, the computer readable program code comprising:
   computer readable program code for detecting the influence of the first defibrillation shock on the patient immediately subsequent to termination of a first defibrillation shock; and computer readable program code for electrically isolating the means for detecting from the means for administering, wherein the detected cardiac activity comprises fibrillation and wherein the computer readable program code for detecting comprises computer readable program code for detecting if the fibrillation ceases immediately after termination of the first defibrillation shock and reinitiates within a predetermined time period after the first defibrillation shock; and computer readable program code for administering a second defibrillation shock having a second shock value that is at least one of substantially equivalent to the first shock value and less than the first shock value immediately if it is determined that the fibrillation has ceased after termination of the first defibrillation shock and reinitiated within the predetermined time period.

84. A computer program product according to claim 83, wherein the computer readable program code for detecting further comprises computer readable program code for detecting the influence of the first defibrillation shock on the patient within about two seconds of termination of the first defibrillation shock.

85. A computer program product according to claim 83, wherein the computer program product further comprises computer readable program code for administering the first defibrillation shock to the patient.

86. A computer program product according to claim 85, wherein the computer program product further comprises computer readable program code for recording the influence of the first defibrillation shock on the patient immediately subsequent to termination of the first defibrillation shock.

87. A computer program product according to claim 86, wherein the computer readable program code for recording comprises computer readable program code for recording the influence of the first defibrillation shock on the patient within about two seconds of termination of the first defibrillation shock.

88. A computer program product according to claim 83, wherein the computer readable program code for detecting further comprises computer readable program code for determining if the cardiac activity of the patient immediately subsequent to termination of a first defibrillation shock is normal cardiac activity.

89. A computer program product according to claim 88, wherein the computer program product further comprises:

computer readable program code for applying a pacing stimulation signal to a heart of a patient it is determined that the cardiac activity of the patient immediately subsequent to termination of the first defibrillation shock is normal cardiac activity.

90. A computer program product of claim 89, wherein the computer readable program code for applying pacing stimulation further comprises computer readable program code for applying the pacing stimulation within about two seconds of termination of the defibrillation shock.

91. A computer program product of claim 90, wherein the computer readable program code that applies the defibrillation shock further comprises computer readable program code that applies to a heart of a patient using at least one first set of electrodes and wherein the computer readable program code that applies pacing stimulation further comprises computer readable program code that applies the pacing stimulation signal to the heart of the patient subsequent to termination of the defibrillation shock using at least one second set of electrodes, wherein the first set of electrodes and the second set of electrodes are the same set of electrodes.

92. A computer program product of claim 89, wherein the pacing stimulation signal comprises single pacing stimulation.

93. A computer program product of claim 89, wherein the pacing stimulation signal comprises paired pacing stimulation.

94. A computer program product of claim 93, wherein the computer readable program code that applies pacing stimulation further comprises computer readable program code that detects cardiac activity of the heart associated with application of the single pacing stimulation and selectively applies paired pacing stimulation based on the detected cardiac activity.

95. A computer program product of claim 94, wherein the computer readable program code that applies further comprises computer readable program code that detects cardiac activity of the heart and selectively applies paired pacing stimulation based on the detected cardiac activity.

96. A computer program product of claim 89, wherein the computer readable program code that applies further comprises computer readable program code that detects a signal specifying application of paired pacing and selectively applies paired pacing stimulation based on the detected signal.

97. A computer program product of claim 96, wherein the defibrillation shock is applied to a heart of a patient using at least one first set of electrodes and wherein the computer readable program code that applies the pacing stimulation further comprises computer readable program code that applies the pacing stimulation signal to the heart of the patient subsequent to termination of the defibrillation shock using at least one second set of electrodes, wherein the first set of electrodes and the second set of electrodes are different sets of electrodes.

98. A computer program product of claim 89, wherein the computer readable program code that applies further comprises computer readable program code that selectively applies paired pacing stimulation to the heart based on at least one of receipt of an external specification and sensed variables associated with cardiac activity.

99. A computer program product of claim 98, wherein the sensed variables associated with cardiac activity comprise a pulse pressure below a predefined threshold.

100. A computer program product of claim 98, wherein the external specification comprises instruction from a healthcare provider.

101. A computer program product according to claim 89, wherein the computer readable program code that applies a pacing stimulation further comprises:

computer readable program code that detects cardiac activity and/or function in the heart;

computer readable program code that selects a type of pacing stimulation to apply to the heart of the patient subsequent to termination of the defibrillation shock based on the detected cardiac activity and/or function; and computer readable program code that applies the selected type of pacing.

102. A computer program product according to claim 101, wherein the computer readable program code that detects cardiac activity and/or function comprises computer readable program code that detects the cardiac activity and/or function before applying a defibrillation shock to a heart of the patient.

103. A computer program product according to claim 101, wherein the computer readable program code that detects cardiac activity and/or function comprises computer readable program code that detects the cardiac activity and/or function after applying a defibrillation shock to a heart of the patient.

104. A computer program product according to claim 101, wherein the selected type of pacing stimulation comprises single pacing stimulation.

105. A computer program product according to claim 101, wherein the selected type of pacing stimulation comprises paired pacing stimulation.

106. A computer program product according to claim 101, wherein the selected type of pacing stimulation comprises a combination of single pacing stimulation and paired pacing stimulation.

107. A computer program product according to claim 89, wherein the computer program code that applies the pacing stimulation further comprises computer readable program code that inhibits application of the pacing stimulation if cardiac activity is detected.

108. A computer program product according to claim 107, wherein the detected cardiac activity comprises a detected blood pressure.

109. A computer program product according to claim 107, wherein the detected cardiac activity comprises spontaneous electrical activity.

110. A computer program product of claim 83, further comprising:
computer readable program code that waits a second predetermined time period if it is determined that the fibrillation ceased after termination of the first defibrillation shock and reinitiated within the first predetermined time period; and
computer readable program code that determines if fibrillation ceases after termination of the second predetermined time period; and
computer readable program code that administers a third defibrillation shock having a third shock value that is at least one of substantially equivalent to the first shock value and less than the first shock value after the second predetermined time period if it is determined that the fibrillation has not ceased after termination of the second predetermined time period.

111. A computer program product according to claim 83, further comprising:
computer readable program code that administers cardiopulmonary resuscitation (CPR) for a second predetermined time period if the fibrillation ceased after termination of the first defibrillation shock and reinitiated within the first predetermined time period;
computer readable program code that determines if the cardiac activity has been influenced by the administration of CPR; and
computer readable program code that administers a third defibrillation shock having a third shock value that is at least one of substantially equivalent to the first shock value and less than the first shock value after termination of the second predetermined time period if it is determined that the fibrillation activity has not been influenced by the administration of CPR during the second predetermined time period.

112. A computer program product according to claim 83, further comprising:
computer readable program code that administers a second defibrillation shock having a second shock value that is higher than the first shock value at the second time if the fibrillation is not influenced by the first defibrillation shock immediately after termination of the first defibrillation shock.

113. A method for detecting the presence of cardiac activity in a patient, comprising:
applying a first defibrillation shock to a heart of the patient; and
detecting the influence of the first defibrillation shock on the patient immediately subsequent to termination of a first defibrillation shock; and
electrically isolating the detector circuit from the first defibrillation shock, wherein the detected cardiac activity comprises fibrillation and wherein the detector circuit is further configured to detect if the fibrillation ceases immediately after termination of the first defibrillation shock and reinitiates within a predetermined time period after the first defibrillation shock; and
applying a second defibrillation shock to the heart of the patient having a second shock value that is at least one of substantially equivalent to the first shock value and less than the first shock value immediately if it is determined that the fibrillation has ceased immediately after termination of the first defibrillation shock and reinitiated within the predetermined time period.

* * * * *

UNITED STATES PATENT AND TRADEMARK OFFICE
CERTIFICATE OF CORRECTION

PATENT NO.        : 7,162,298 B2
APPLICATION NO.   : 10/238340
DATED             : January 9, 2007
INVENTOR(S)       : Ideker et al.

It is certified that error appears in the above-identified patent and that said Letters Patent is hereby corrected as shown below:

On The Title Page

Sec. [74]: Should read: --Myers Bigel Sibley & Sajovec, P.A.--

Column 1,

Line 9-12: Should read: --U.S. patent application Ser. No. 10/238,342 entitled *Methods, Systems and Computer Program Products for Treating Fibrillation in a Patient Based on the Presence of Fibrillation Following Administration of Defibrillation Therapy* (Attorney Docket No. 5656-24) filed--

Column 8,

Line 5-6: Should read: --cation Ser. No. 10/238,343 (Attorney Docket No. 5656-30) entitled *Post-Defibrillation Pacing Methods and Devices*, the disclosure of which is incur- --

Column 24,

Line 51: Should read: --38. A Device according to claim 23, wherein the controller--

Signed and Sealed this

Seventeenth Day of April, 2007

JON W. DUDAS
*Director of the United States Patent and Trademark Office*